(12) United States Patent
Mathiason et al.

(10) Patent No.: US 11,598,783 B1
(45) Date of Patent: Mar. 7, 2023

(54) IN VITRO DETECTION OF PRIONS

(71) Applicants: Candace K. Mathiason, Windsor, CO (US); Edward A. Hoover, Fort Collins, CO (US)

(72) Inventors: Candace K. Mathiason, Windsor, CO (US); Edward A. Hoover, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 17/078,678

(22) Filed: Oct. 23, 2020

Related U.S. Application Data

(60) Provisional application No. 62/925,119, filed on Oct. 23, 2019.

(51) Int. Cl.
*G01N 33/68* (2006.01)

(52) U.S. Cl.
CPC . *G01N 33/6896* (2013.01); *G01N 2333/4709* (2013.01); *G01N 2800/2828* (2013.01)

(58) Field of Classification Search
CPC ....... G01N 33/6896; G01N 2333/4709; G01N 2800/2828
See application file for complete search history.

(56) References Cited

U.S. PATENT DOCUMENTS

| | | | |
|---|---|---|---|
| 5,750,361 | A | 5/1998 | Prusiner et al. |
| 6,211,149 | B1 | 4/2001 | Chesebro et al. |
| 7,351,526 | B2 | 4/2008 | Soto et al. |
| 7,407,760 | B2 | 8/2008 | Supattapone et al. |
| 10,359,434 | B2 | 7/2019 | Hoover et al. |
| 2002/0004586 | A1 | 1/2002 | Aguzzi et al. |
| 2005/0255525 | A1 | 11/2005 | Bastian |
| 2005/0266412 | A1 | 12/2005 | Prusiner |
| 2006/0040260 | A1 | 2/2006 | Baskakov |
| 2006/0263767 | A1 | 11/2006 | Castrillon et al. |
| 2008/0118938 | A1 | 5/2008 | Estrada et al. |
| 2009/0047696 | A1 | 2/2009 | Caughey et al. |
| 2011/0311997 | A1 | 12/2011 | Soto et al. |
| 2016/0116487 | A1 | 4/2016 | Hoover et al. |
| 2016/0320413 | A1 | 11/2016 | Jackson et al. |

FOREIGN PATENT DOCUMENTS

WO    WO2013056841 A1    4/2013

OTHER PUBLICATIONS

Denkers et al., J. Gen. Virol., 2016, 97:2023-9.*
Henderson et al., PLoS, 2013, 8(9):e74377.*
Miller et al., J. Virol., 2011, 85(6):2813-7.*
Elder et al., J. Virol., 2015, 89(14):7421-4.*
Bannach et al., PLoS One, 2012, 7(5):e36620.*
Elder et al., 2013, PLoS One, 8(11): e80203.*

Mathiason CK, Powers JG, Dahmes SJ, Osborn DA, Miller KV, Warren RJ, Mason GL, Hays SA, Hayes-Klug J, Seelig DM, Wild MA, Wolfe LL, Spraker TR, Miller MW, Sigurdson CJ, Telling GC, Hoover EA. Infectious prions in the saliva and blood of deer with chronic wasting disease. Science. Oct. 6, 2006;314(5796):133-6. doi: 10.1126/science.1132661. PMID:17023660.

Murayama Y, Yoshioka M, Okada H, Takata M, Yokoyama T, Mohri S. Urinary excretion and blood level of prions in scrapie-infected hamsters. J Gen Virol. 2007;88(Pt 10):2890-2898. doi:10.1099/vir. 0.82786-0.

Houston F, McCutcheon S, Goldmann W, et al. Prion diseases are efficiently transmitted by blood transfusion in sheep. Blood. 2008;112(12):4739-4745. doi:10.1182/blood-2008-04-152520.

Orrú CD, Wilham JM, Hughson AG, et al. Human variant Creutzfeldt-Jakob disease and sheep scrapie PrP(res) detection using seeded conversion of recombinant prion protein. Protein Eng Des Sel. 2009;22(8):515-521. doi:10.1093/protein/gzp031.

Castilla J, Saá P, Hetz C, Soto C. In vitro generation of infectious scrapie prions. Cell. 2005;121(2):195-206. doi:10.1016/j.cell.2005. 02.011.

Terry, L. A., et al. "Detection of PrPsc in blood from sheep infected with the scrapie and bovine spongiform encephalopathy agents." Journal of virology 83.23 (2009): 12552-12558.

D'Castro L, Wenborn A, Gros N, et al. Isolation of proteinase K-sensitive prions using pronase E and phosphotungstic acid. PLoS One. 2010;5(12):e15679. Published Dec. 20, 2010. doi:10.1371/journal.pone.0015679.

McCutcheon S, Alejo Blanco AR, Houston EF, et al. All clinically-relevant blood components transmit prion disease following a single blood transfusion: a sheep model of vCJD. PLoS One. 2011;6(8):e23169. doi:10.1371/journal.pone.0023169.

Bannach O, Birkmann E, Reinartz E, et al. Detection of prion protein particles in blood plasma of scrapie infected sheep. PLoS One 2012;7(5):e36620. doi:10.1371/journal.pone.0036620.

Lacroux C, Bougard D, Litaise C, et al. Impact of leucocyte depletion and prion reduction filters on TSE blood borne transmission. PLoS One. 2012;7(7):e42019. doi:10.1371/journal.pone. 0042019.

(Continued)

*Primary Examiner* — Olga N Chernyshev
(74) *Attorney, Agent, or Firm* — Michael M. McGaw; McGaw Law, P.C.

(57) ABSTRACT

A method for the pre-amplification sample processing of a prion or other amyloid converting protein in a sample. A key feature of the assay is its ability to amplify and thus detect small quantities of the abnormally folded 'seed' forms of misfolded proteins. The assay also opens up the ability to quantify the amount of "seed" present. The methods facilitate the early detection of diseases associated with misfolded proteins, as well as assessment of therapies against these diseases. The method can detect amyloid seeding activity (prions) in blood samples, including the buffy coat cells harvested from pre-clinical and clinical subjects. These findings further enhance the ability to assess the longitudinal course of prion disease and the role hematogenous prions play in pathogenesis. We demonstrate the ability to detect prions in as few as $5 \times 10^5$ buffy coat cells by lipase-iron oxide bead-RT-QuIC performed at 42° C. (LIQ42) in 79% of CWD-biopsy positive WTD, which increased to 100% when LIQ was performed at 55° C. (LIQ55). RT-QuIC assessment of PMCA (PQ) round 5 product revealed hematogenous prions in 92% of the WTD.

18 Claims, 25 Drawing Sheets

(56) References Cited

OTHER PUBLICATIONS

Wilham JM, Orrú CD, Bessen RA, et al. Rapid end-point quantitation of prion seeding activity with sensitivity comparable to bioassays. PLoS Pathog. 2010;6(12):e1001217. Published Dec. 2, 2010. doi:10.1371/journal.ppat.1001217.

Orrú CD, Wilham JM, Raymond LD, et al. Prion disease blood test using immunoprecipitation and improved quaking-induced conversion. mBio 2011;2(3):e00078-e11. Published May 10, 2011. doi:10.1128/mBio.00078-11.

Orrù CD, Wilham JM, Vascellari S, Hughson AG, Caughey B. New generation QuIC assays for prion seeding activity. Prion. 2012;6(2):147-152. doi:10.4161/pri.19430.

Gonzalez-Romero D, Barria MA, Leon P, Morales R, Soto C. Detection of infectious prions in urine. FEBS Lett. 2008;582(21-22):3161-3166. doi: 10.1016/j.febslet.2008.08.003.

Morales R, Buytaert-Hoefen KA, Gonzalez-Romero D, et al. Reduction of prion infectivity in packed red blood cells. Biochem Biophys Res Commun. 2008;377(2):373-378. doi:10.1016/j.bbrc.2008.09.141.

Chen B, Morales R, Barria MA, Soto C. Estimating prion concentration in fluids and tissues by quantitative PMCA. Nat Methods. 2010;7(7):519-520. doi:10.1038/nmeth.1465.

Barria MA, Gonzalez-Romero D, Soto C. Cyclic amplification of prion protein misfolding. Methods Mol Biol. 2012;849:199-212. doi:10.1007/978-1-61779-551-0_14.

Wroe SJ, Pal S, Siddique D, et al. Clinical presentation and pre-mortem diagnosis of variant Creutzfeldt-Jakob disease associated with blood transfusion: a case report. Lancet. 2006;368(9552):2061-2067. doi:10.1016/S0140-6736(06)69835-8.

Edgeworth JA, Farmer M, Sicilia A, et al. Detection of prion infection in variant Creulzfeldt-Jakob disease: a blood-based assay. Lancet. 2011;377(9764):487-493. doi:10.1016/S0140-6736(10)62308-2.

Group, U.B.S.P.W. Creutzfeldt-Jakob Disease: Joint UKBTS / HPA Profession Advisory Committee Position Statement 2020.

Andréoletti O, Litaise C, Simmons H, et al. Highly efficient prion transmission by blood transfusion. PLoS Pathog. 2012;8(6):e1002782 doi:10.1371/journal.ppat.1002782.

Soto, Claudio, et al. "Pre-symptomatic detection of prions by cyclic amplification of protein misfolding." FEBS letters 579.3 (2005): 638-642.

Saá P, Castilla J, Soto C. Presymptomatic detection of prions in blood. Science. 2006;313(5783):92-94. doi:10.1126/science.1129051.

Atarashi R, Moore RA, Sim VL, et al. Ultrasensitive detection of scrapie prion protein using seeded conversion of recombinant prion protein. Nat Methods. 2007;4(8):645-650. doi:10.1038/nmeth1066.

Castilla J, Saá P, Soto C. Detection of prions in blood. Nat Med. 2005;11(9):982-985. doi:10.1038/nm1286.

Glier H, Holada K. Blood storage affects the detection of cellular prion protein on peripheral blood leukocytes and circulating dendritic cells in part by promoting platelet satellitism. J Immunol Methods. 2012;380(1-2):65-72. doi:10.1016/j.jim.2012.04.002.

Saá P, Castilla J, Soto C. Cyclic amplification of protein misfolding and aggregation. Methods Mol Biol. 2005;299:53-65. doi:10.1385/1-59259-874-9:053.

Yokoyama T, Takeuchi A, Yamamoto M, Kitamoto T, Ironside JW, Morita M. Heparin enhances the cell-protein misfolding cyclic amplification efficiency of variant Creutzfeldt-Jakob disease. Neurosci Lett. 2011;498(2):119-123. doi:10.1016/j.neulet.2011.04.072.

Elder AM, Henderson DM, Nalls AV, Wilham JM, Caughey BW, et al. (2013) In Vitro Detection of prionemia in TSE-Infected Cervids and Hamsters. PLOS One 8(11): e80203.

Smith CB, Booth CJ, Pedersen JA. Fate of prions in soil: a review. J Environ Qual. 2011;40(2):449-461. doi:10.2134/eq2010.0412.

Properzi F, Badhan A, Klier S, et al. Physical, chemical and kinetic factors affecting prion infectivity. Prion. 2016;10(3):251-261. doi:10.1080/19336896.2016.1181250.

Group, U.B.S.P.W. Creulzfeldt-Jakob Disease: Joint UKBTS / HPA Professional Advisory Committee Position Statement. 2015. http://www.transfusionguidelines.org/document-library/documents/jpac-position-statement-vcjd-may-2015/download-file/Position%20Statement%20on%20vCJD%20May%202015.pdf.

Cali, I., Puoti, G., Smucny, J. et al. Co-existence of PrPD types 1 and 2 in sporadic Creutzfeldt-Jakob disease of the VV subgroup: phenotypic and prion protein characteristics. Sci Rep 10, 1503 (2020). https://doi.org/10.1038/s41598-020-58446-0.

Elder AM, Henderson DM, Nalls AV, et al. Immediate and Ongoing Detection of Prions in the Blood of Hamsters and Deer following Oral, Nasal, or Blood Inoculations. J Virol. 2015;89(14):7421-7424. doi:10.1128/JV1.00760-15.

Cooper SK, Hoover CE, Henderson DM, Haley NJ, Mathiason CK, Hoover EA. Detection of CWD in cervids by RT-QuIC assay of third eyelids. PLoS One. 2019;14(8):e0221654. Published Aug. 28, 2019. doi:10.1371/journal.pone.0221654.

Mathiason CK, Hayes-Klug J, Hays SA, et al. B cells and platelets harbor prion infectivity in the blood of deer infected with chronic wasting disease. J Virol. 2010;84(10):5097-5107. doi:10.1128/JVI.02169-09.

Mathiason CK. Silent Prions and Covert Prion Transmission. PLoS Pathog. 2015;11(12):e1005249. Published Dec. 10, 2015. doi:10.1371/journal.ppat.1005249.

Tennant, J. M., Li, M., Henderson, D. M., Tyer, M. L., Denkers, N. D., Haley, N. J., Mathiason, C. K., & Hoover, E. A. (2020). Shedding and stability of CWD prion seeding activity in cervid feces. PloS one, 15(3), e0227094. https://doi.org/10.1371/journal.pone.0227094.

Luk, C. C., Mathiason, C. K., Orrù, C. D., Jansen, G. H., Thiele, A., Caughey, B., & Sim, V. L. (2021). Creutzfeldt-Jakob disease in pregnancy: the use of modified RT-QuIC to determine infectivity in placental tissues. Prion, 15(1), 107-111. https://doi.org/10.1080/19336896.2021.1933872.

Denkers, N. D., Henderson, D. M., Mathiason, C. K., & Hoover, E. A. (2016). Enhanced prion detection in biological samples by magnetic particle extraction and real-time quaking-induced conversion. The Journal of general virology, 97(8), 2023-2029. https://doi.org/10.1099/jgv.0.000515.

McNulty, E. E., Nalls, A. V., Xun, R., Denkers, N. D., Hoover, E. A., & Mathiason, C. K. (2020). In vitro detection of haematogenous prions in white-tailed deer orally dosed with low concentrations of chronic wasting disease. The Journal of general virology, 101(3), 347-361. https://doi.org/10.1099/jgv.0.001367.

McNulty, E., Nalls, A. V., Mellentine, S., Hughes, E., Pulscher, L., Hoover, E. A., & Mathiason, C. K. (2019). Comparison of conventional, amplification and bio-assay detection methods for a chronic wasting disease inoculum pool. PloS one, 14(5), e0216621. https://doi.org/10.1371/journal.pone.0216621.

\* cited by examiner

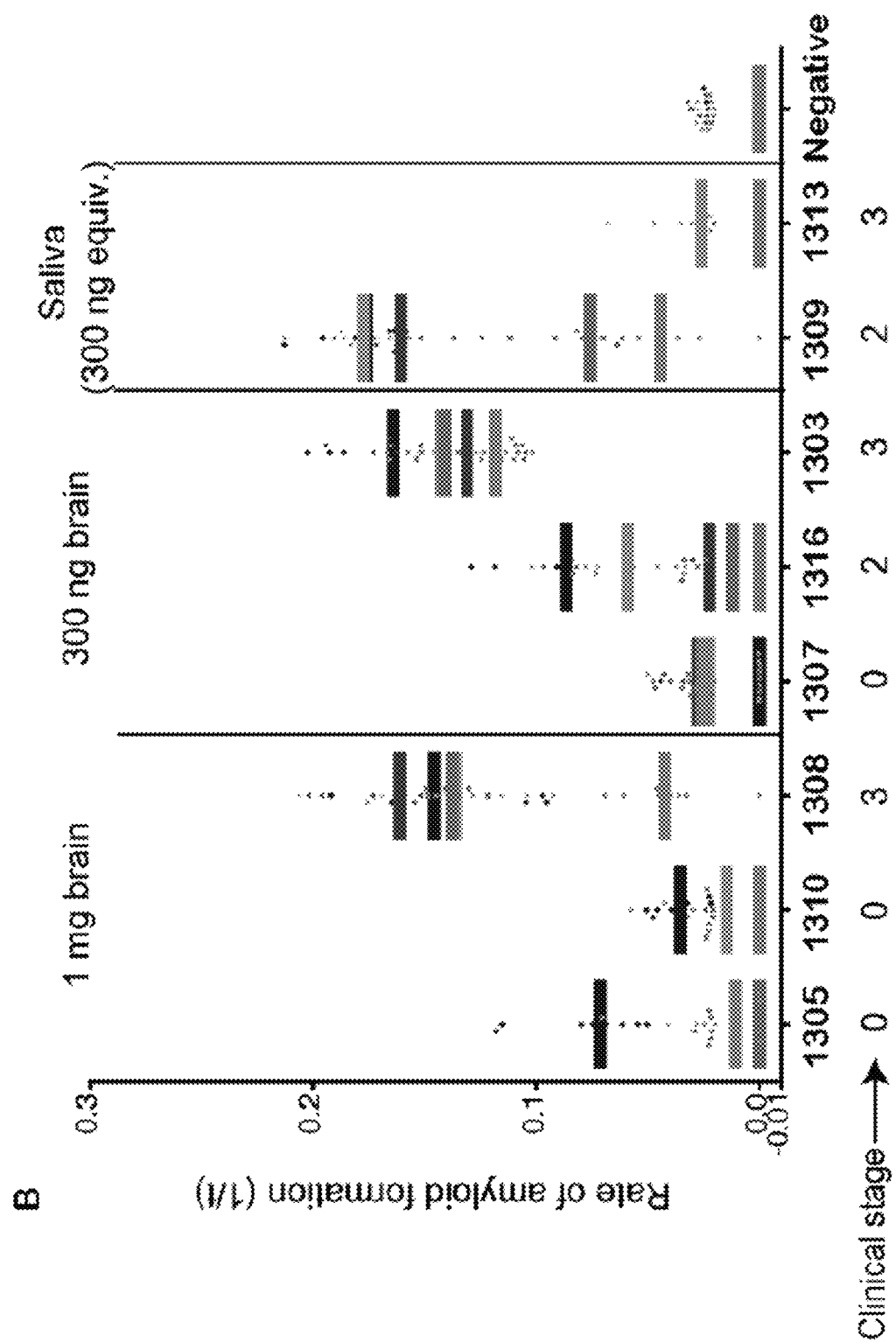
FIG. 3 - continued

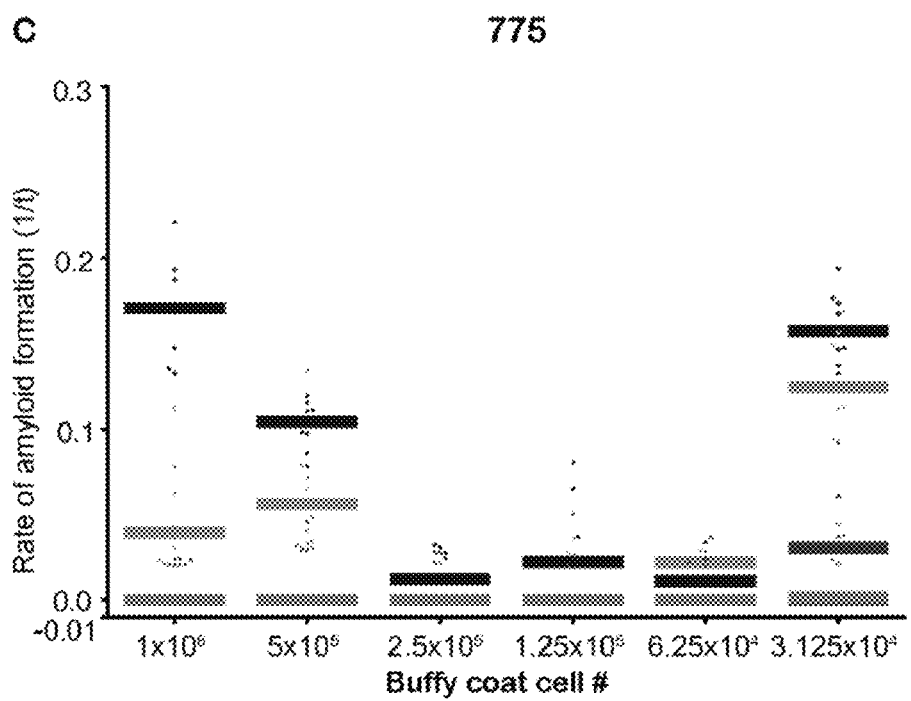
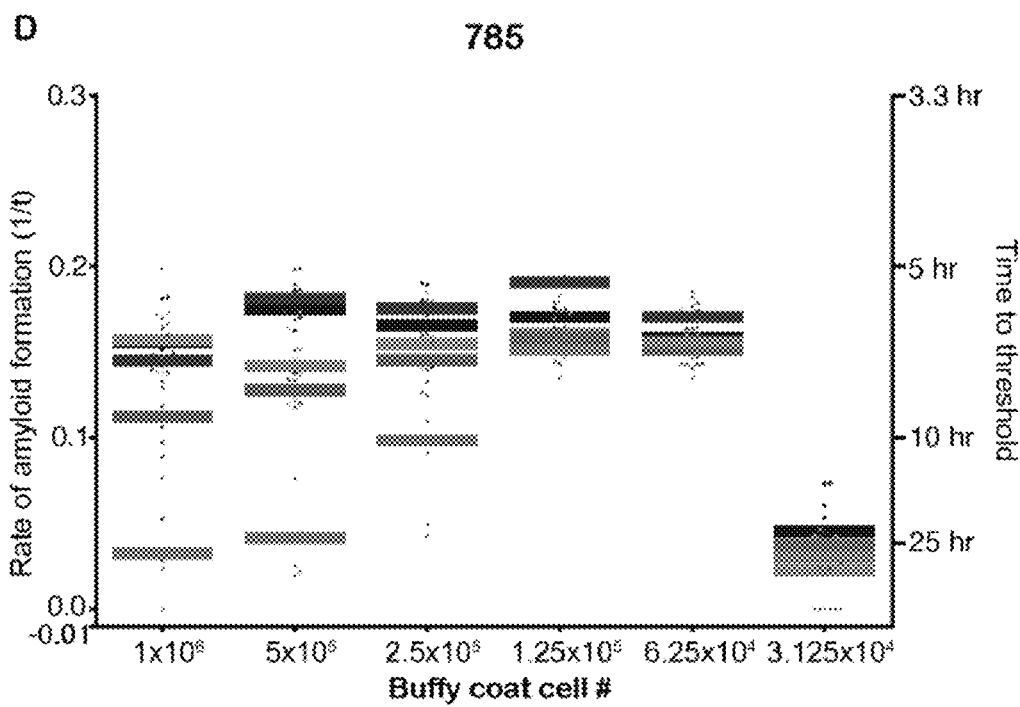
FIG. 4 - continued

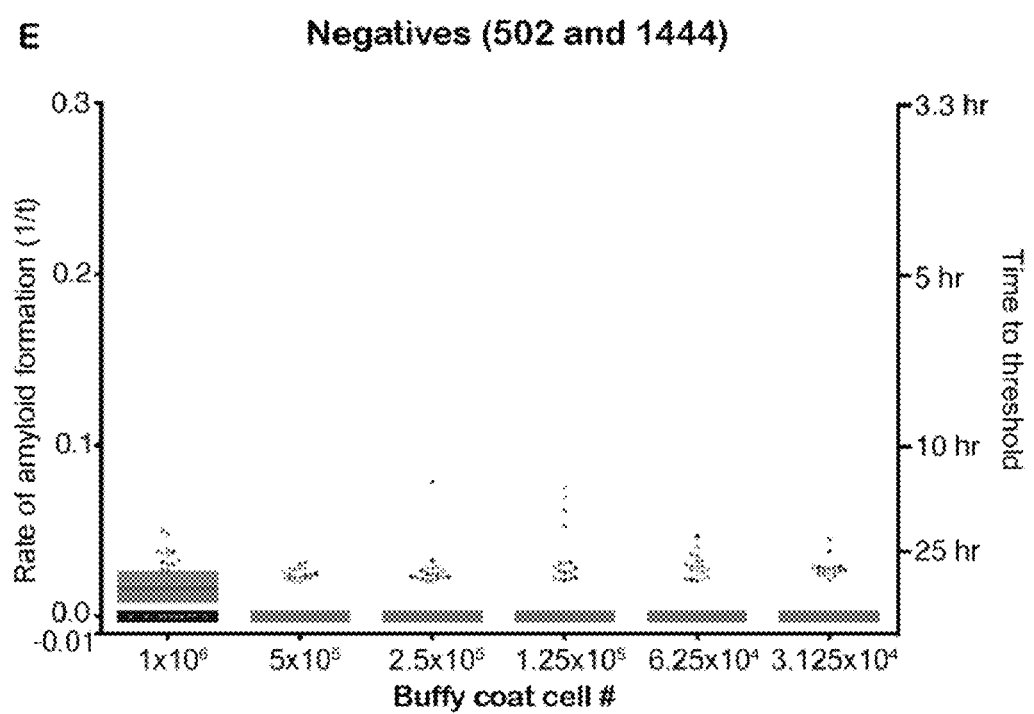
*FIG. 4 - continued*

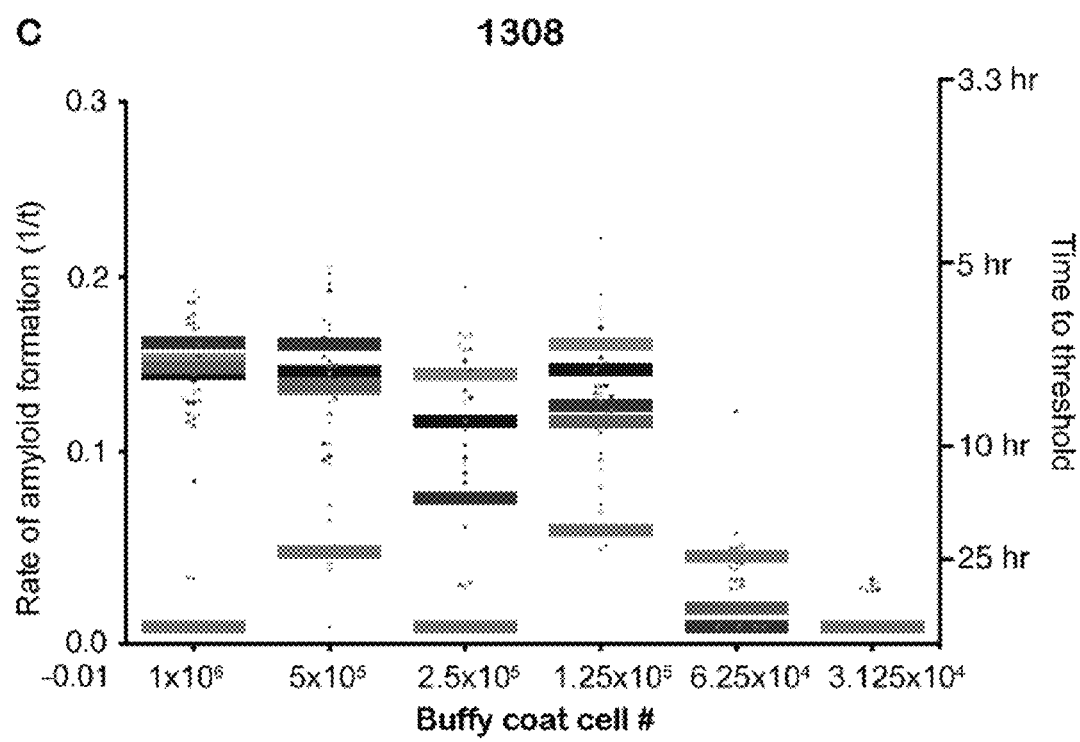
FIG. 5 - continued

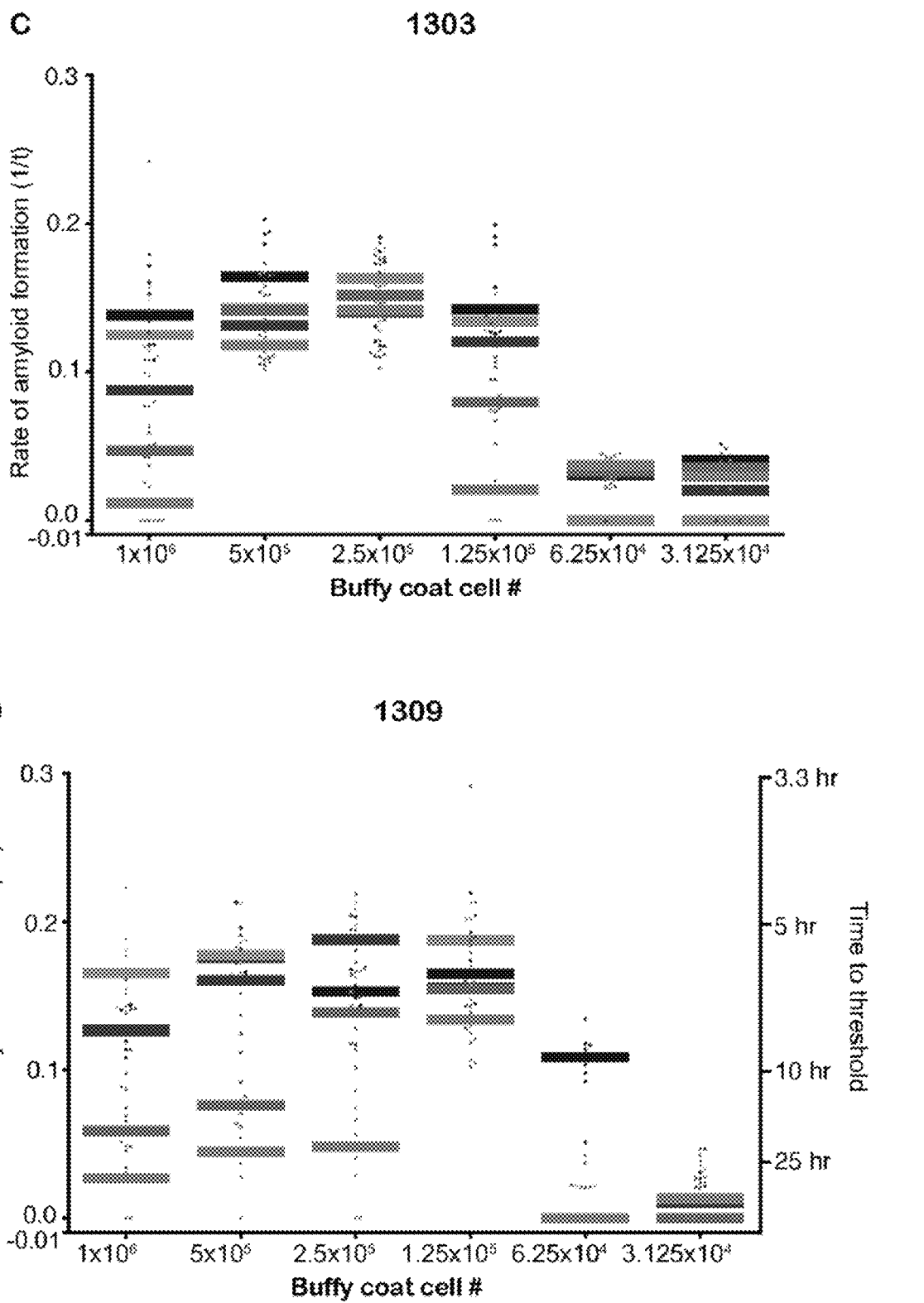
FIG. 6 - continued

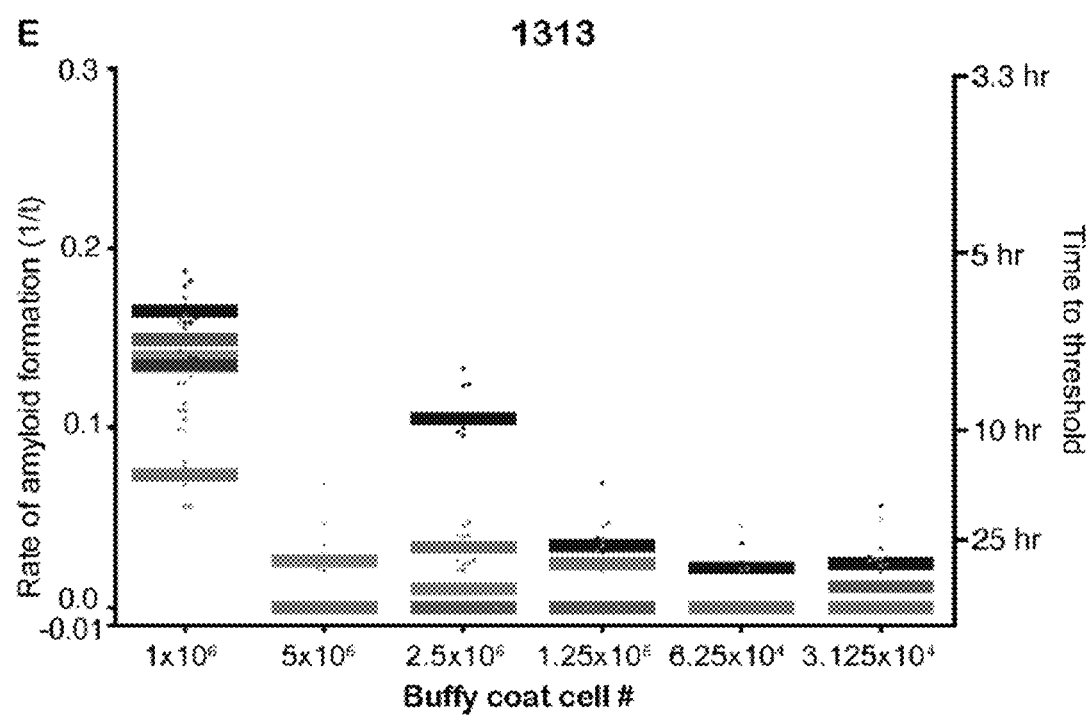
FIG. 6 - continued

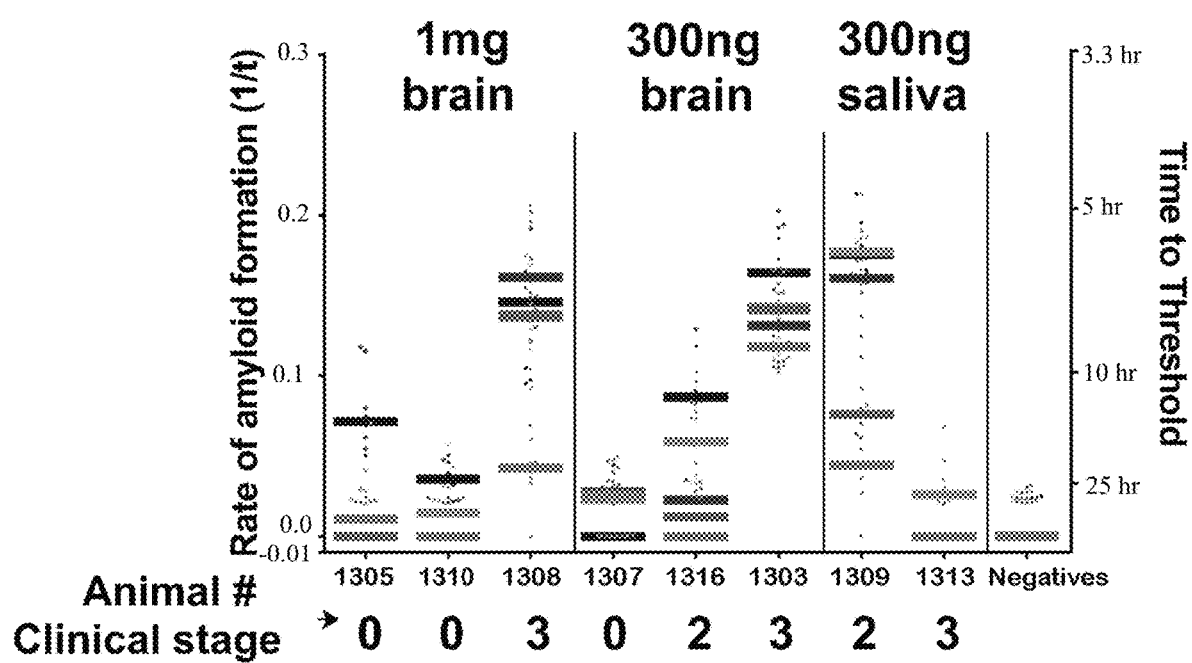
FIG. 12 - continued

*FIG. 16*

IN VITRO DETECTION OF PRIONS

CROSS-REFERENCE TO RELATED APPLICATIONS

This application claims the benefit of U.S. Provisional Application No. 62/925,119, filed Oct. 23, 2019.

STATEMENT OF GOVERNMENT INTEREST

This invention was made with government support under grant numbers R01 NS061902, N01 AI025491, R01 AI093634, R01 AI112956 awarded by the National Institutes of Health. The government has certain rights in the invention.

FIELD OF INVENTION

This invention relates to screening and diagnoses of neurodegenerative diseases. More specifically, this invention relates to the detection and quantification of misfolded proteins associated with neurodegenerative diseases.

BACKGROUND OF THE INVENTION

Blood contains the infectious agent associated with prion disease affecting several mammalian species, including humans (Creutzfeldt-Jakob disease or CID), cervids (chronic wasting disease, CWD), sheep (scrapie), and cattle (bovine spongiform encephalopathy, BSE). Bioassays of blood components in transgenic mice, hamsters, transgenic drosophila, and ruminant species have confirmed that sufficient prion agent is present in the blood of both symptomatic and asymptomatic carriers to transmit these fatal neurodegenerative diseases.

Public health concern was raised when retrospective studies affirmed that as many as 1 in 2000 individuals in the UK may be asymptomatic carriers of variant (v)CJD, the human prion disease attributed to presumed oral BSE exposure. Furthermore, prion infectivity has been demonstrated in blood and bone marrow of patients that have the spontaneous form of the disease, sporadic (s)CJD, which affects 1 in a million humans worldwide.

These findings suggest that the presence of hematogenous prions, or prionemia, in a cross-section of the population, has the potential of entering the blood donor pool or being unwittingly transferred during surgical interventions.

Given the litany of issues arising from BSE contaminating the meat supply in the UK, a growing public concern about CWD cervid infections is its zoonotic potential. While no human cases of prion disease have been reported in association with CWD exposure, the zoonotic potential of CWD remains unknown. Experimental studies in non-human primates, as well as in vitro assessment of conversion competence in amplification assays remain equivocal. Contributing to the increased concern is the progressive geographical spread, host range expansion and population decline reported in cervid populations affected by CWD. Pre-2000 the disease was thought to be a regional disease, confined to free-range and captive herds in the North American Rocky Mountain region. However, CWD has now been detected in 26 US states, 3 Canadian provinces, the Korean peninsula and Scandinavia.

Minimally invasive methods to identify CWD infected hosts are of paramount importance. Minimally invasive methods are also needed to identify CJD, CWD, BSE, scrapie, and other prion diseases in hosts. To date, postmortem testing of brain or lymphoid tissues by immunohistochemistry is the gold standard to assess prion status. Immunohistochemistry performs well for the detection of prions in lymphoid tissues harboring relatively high prion burdens, but lacks adequate repeat sample access and sensitivity to identify early pre-clinical infections. To this end, efforts are ongoing to develop antemortem surveillance tests incorporating various biological tissues and fluids known to contain infectivity. Longitudinal blood sampling provides an easily accessed self-replenishing bodily fluid containing the prion agent. Bioassay has shown blood of CWD-infected cervids (clinical and pre-clinical) contain infectivity. Yet, the ability to detect blood-borne prions by in vitro methods remains difficult.

SUMMARY OF THE INVENTION

In vitro detection of hematogenous prions is hampered by low circulating levels and/or blood-associated inhibitors. Further refinement of the amplification assays, e.g. protein misfolding cyclic amplification (PMCA) and real time quaking induced conversion (RT-QuIC), address aspects of these obstacles. The use of these methods has led to improved detection of amyloid seeding activity in tissues, bodily fluids and the environments of prion-infected hosts. Both PMCA and RT-QuIC have utility in demonstrating prions in blood components harvested from sheep, cervids, rodents, and humans.

A variety of pre-amplification strategies, including sodium phosphotungstate (NaPTA) precipitation, PrP antibody-tagging, beads and lipase treatment, as well as combined use of amplification assays, can be used to enhance detection of prions prior to the onset of clinical disease. Methodologies are taught herein for pre-amplification sample processing including enzyme treatment (Lipase), metal bead extraction (Iron oxide beads) with RT-QuIC readout (LIQ), and combined use of PMCA and RT-QuIC (PQ) to assess prion burdens in buffy coat cells harvested from white-tailed deer (WTD). The WTD were orally dosed with 1 g, 1 mg, or 300 ng CWD+ brain homogenate or 30 ml of CWD+ saliva containing 300 ng brain equivalent seeding activity in RT-QuIC (henceforth referred to as 300 ng CWD+ saliva equivalent).

We demonstrate: (i) amyloid seeding activity (prions) in buffy coat cells harvested from pre-clinical and clinical CWD positive WTD, (ii) the ability to detect prions in buffy coat blood cells harvested from deer orally dosed with low concentrations (e.g. 300 ng) CWD positive brain or saliva, and (iii) detection of prions in as few as $5 \times 10^5$ buffy coat cells harvested from pre-clinical CWD positive WTD. These findings further enhance the ability to assess the longitudinal course of prion disease and the role hematogenous prions play in pathogenesis.

We demonstrate the ability to detect prions in as few as $5 \times 10^5$ buffy coat cells by lipase-iron oxide bead-RT-QuIC performed at 42° C. (LIQ42) in 79% of CWD-biopsy positive WTD, which increased to 100% when LIQ was performed at 55° C. (LIQ55). RT-QuIC assessment of PMCA (PQ) round 5 product revealed hematogenous prions in 92% of the WTD.

In a first aspect the present invention provides a method of pre-amplification sample processing of an amyloid converting protein in a sample, such as a blood sample and most particularly the buffy coat fraction of a blood sample. The method can include the steps of providing a sample (e.g. blood sample, buffy coat fraction of a blood sample) to be processed for the screening of amyloid converting protein, performing lipase treatment of the sample, performing metal bead extraction on the lipase-treated sample using iron oxide magnetic beads (e.g. superparamagnetic iron oxide beads (IOBs)), recovering the bead fraction of the lipase-treated sample, and resuspending the resulting beads to yield a processed sample. While not wishing to be bound to any theory, it appears that the octarepeat section of the prion binds to the iron oxide bead (e.g. uncoated IOB). Further, red bloods in the reaction mixture appear to inhibit actually inhibit the conversion process that permits amplification of sufficient amyloid fibrils for detection. The inhibition may be due to heme interference.

Real time quaking induced conversion can be performed on the processed sample at about at 42° C. or higher. In an advantageous embodiment, the method according to the first aspect can further include the step of performing real time quaking induced conversion on the processed sample at about at 42° C. or higher, at about 45° C. or higher, at about 47° C. or higher, at about 50° C. or higher, at about 52° C. or higher, or at about 55° C. or higher. In a particularly advantageous embodiment, the method according to the first aspect can further include the step of performing real time quaking induced conversion on the processed sample at about at 55° C. or higher.

The sample according to the first aspect can be a blood sample. In an advantageous embodiment the blood sample is collected in an anticoagulant, such as heparin or CPDA. CDPA is a particularly advantageous anticoagulant. In further particularly advantageous aspects the blood sample is a buffy coat cell fraction from a blood sample.

PMCA or RT-QuIC can be performed on the processed sample. In certain advantageous embodiments, the method according to the first aspect can include the steps of amplifying the processed sample using protein misfolding cyclic amplification (PMCA) and analyzing the amplified sample using real time quaking induced conversion readout. A plurality of rounds of PMCA can be performed to amplify the sample. For example, 2 or more rounds of PMCA, 3 or more rounds of PMCA are performed, or 4 or more rounds of PMCA can be performed. In a particularly advantageous embodiment, 5 or more rounds of PMCA are performed.

In a second aspect the invention provides a method for the amplification of a prion disease-associated isoform of prion protein ($PrP^D$) in a sample. The method according to the second aspect can include the steps of providing a sample (e.g. a sample of RBCs or the buffy coat fraction of a blood sample) having a $PrP^D$ or a sample to be screened for the presence of $PrP^D$, performing lipase treatment of the sample, performing metal bead extraction (e.g. with IOBs) on the lipase-treated sample, whereby the metal bead extraction yields an extracted sample, providing a reaction mixture comprising an excess of native conformation protein ($PrP^C$), contacting the reaction mix with the extracted sample, incubating the reaction mixture under conditions effective to cause misfolding or aggregation of the $PrP^C$ in the reaction mixture, disaggregating any aggregates of $PrP^D$ formed during the incubating step, and repeating the incubating and disaggregating steps one or more times to produce an amplified $PrP^D$ in the reaction mixture. the aggregates can be disaggregated by a techniques such as sonication, stirring, shaking, freezing/thawing, laser irradiation, high pressure, homogenization, cyclic agitation or a combination of the aforementioned.

The method according to the second aspect can further include the steps of incubating the reaction mixture in the presence of thioflavin-T under conditions effective to cause aggregation of the $PrP^D$ in the reaction mixture and binding of the thioflavin-T to the resulting aggregates and measuring the fluorescence in the reaction mixture. The fluorescence in the reaction mixture is indicative of the presence or amount of amyloidogenic $PrP^D$ in the sample to be screened for the presence of $PrP^D$. In an advantageous embodiment methods employing thioflavin-T can include the steps of comparing the fluorescence in the reaction mix to a standard curve of known concentration and computing the amount of $PrP^D$ seed in the sample based upon the comparison.

The method according to the second aspect can be used, for example, on a sample that is being screened for a misfolded protein caused by a disease or disorder including CJD, CWD, BSE, scrapie, Alzheimer's Disease, Parkinson's Disease, Amyotrophic Lateral Sclerosis, Chronic Traumatic Encephalopathy, Fronto-Temporal Dementia, Prion Mutation Carriers, and System Atrophy.

In an advantageous embodiment, the method according to the second aspect can further include the step of performing real time quaking induced conversion on the processed sample at about at 42° C. or higher, at about 45° C. or higher, at about 47° C. or higher, at about 50° C. or higher, at about 52° C. or higher, or at about 55° C. or higher. In a particularly advantageous embodiment, the method according to the first aspect can further include the step of performing real time quaking induced conversion on the processed sample at about at 55° C. or higher.

In a third aspect the invention provides a method for the detection of an amyloid converting protein in a whole blood sample. The method according to the third aspect can include the steps of collecting a sample to be processed for the screening of amyloid converting protein, (optionally wherein the sample is combined with CPDA-1 or other anticoagulant), freezing and thawing the sample (and/or performing lipase treatment of the sample), performing metal bead extraction on the thawed sample using magnetic iron oxide beads (IOBs), recovering the bead fraction of the extracted sample, amplifying the sample using a plurality of PMCA reactions with substrate, (optionally) transferring the amplified sample to a multi-well plate, combining the transferred sample with substrate and Thioflavin T, amplifying the sample using an RT-QuIC reaction, and detecting the presence of amyloid converting protein in the whole blood sample by measuring the resulting fluorescence in the sample.

In a fourth aspect the invention provides a second method for the detection of an amyloid converting protein in a sample. The method according to the fourth aspect can include the steps of collecting a sample to be processed for the screening of amyloid converting protein, freezing and thawing the sample (and/or performing lipase treatment of the sample), performing metal bead extraction on the thawed sample using magnetic iron oxide beads (IOBs), recovering the bead fraction of the extracted sample, amplifying the sample using a plurality of PMCA reactions with substrate, optionally transferring the amplified sample to a multi-well plate, combining the transferred sample with substrate and Thioflavin T, amplifying the sample using an RT-QUIC reaction and detecting the presence of amyloid converting protein in the whole blood sample by measuring the resulting fluorescence in the sample. In an advantageous embodiment the sample is a blood sample, a urine sample, and a saliva sample. In a particularly advantageous embodiment the sample is a buffy coat fraction of a blood sample. The plurality of PMCA amplification rounds can be performed comprising the steps of transferring a portion of PMCA amplified sample to fresh NBH, sonicating the sample and incubating the sample under conditions effective to cause the conversion of substrate in the sample. The plurality of PMCA amplification rounds can comprise 2 or more rounds of PMCA amplification, 3 or more rounds PMCA of amplification, 4 or more rounds PMCA of amplification, or 5 or more rounds PMCA of amplification.

In a fifth aspect the invention provides a method for the detection of prions in a sample. The method according to the fifth aspect can include the steps of providing a sample having about buffy coat cells (e.g. about $5 \times 10^5$ buffy coat cells), performing lipase treatment on the sample, extracting the sample using iron oxide bead beads, performing RT-QuIC on the sample at about 42° C. (LIQ42) or higher.

In a sixth aspect the invention provides a second method for the detection of prions in a sample. The method according to the sixth aspect can include the steps of providing a sample having about buffy coat cells (e.g. about $5 \times 10^5$ buffy coat cells), performing lipase treatment on the sample, extracting the sample using iron oxide bead beads, performing RT-QuIC on the sample at about 55° C. (LIQ55) or higher.

In a seventh aspect the invention provides a third method for the detection of prions in a sample. The method according to the seventh aspect can include the steps of providing a sample having about $1 \times 10^4$ to about $1 \times 10^6$ buffy coat cells, performing lipase treatment on the sample, extracting the sample using iron oxide bead beads and performing RT-QuIC on the sample at about 55° C. (LIQ55) or higher.

BRIEF DESCRIPTION OF THE DRAWINGS

For a fuller understanding of the invention, reference should be made to the following detailed description, taken in connection with the accompanying drawings, in which:

Figure 16:
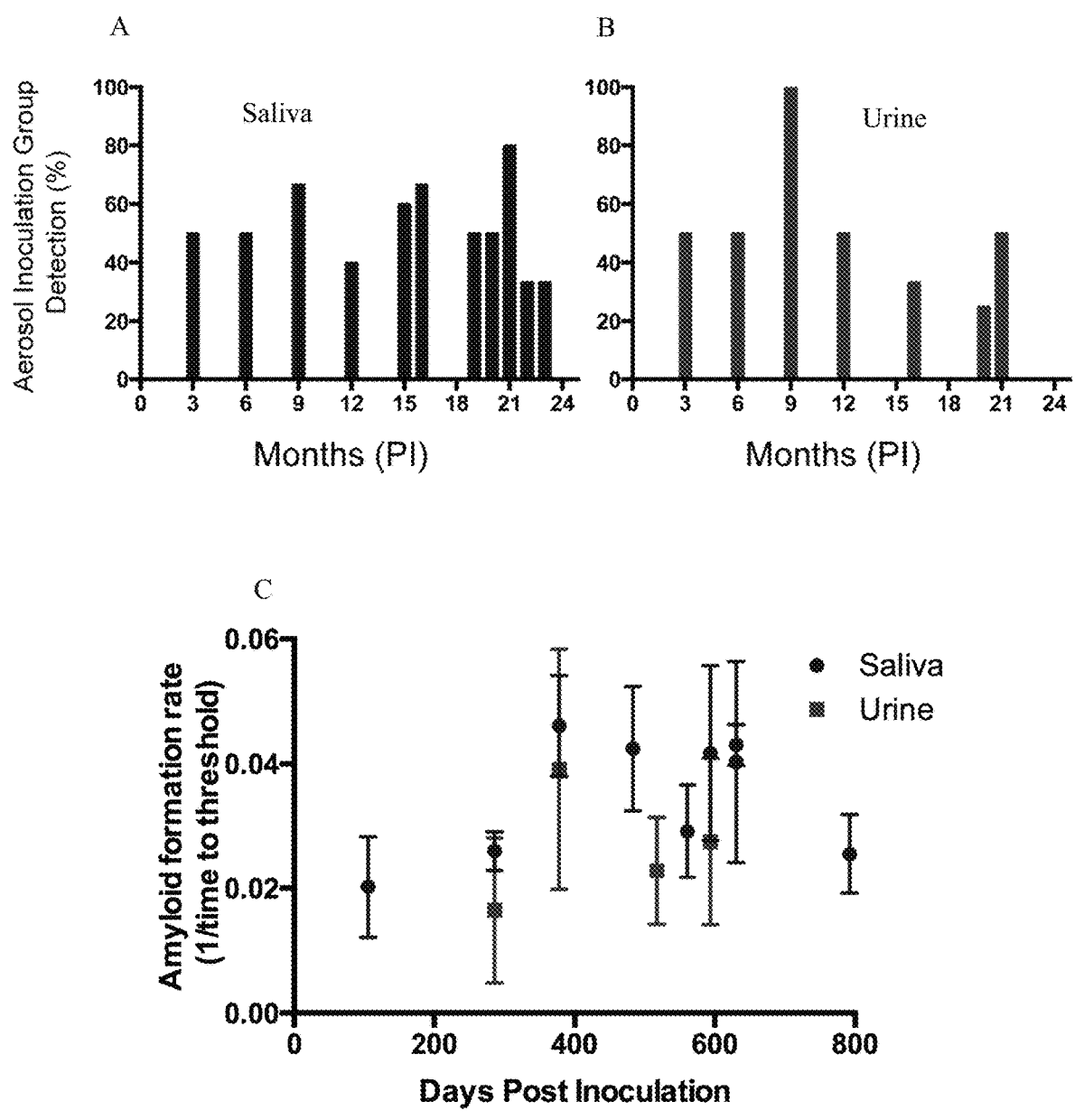

FIG. 16 is a set of three graphs showing longitudinal detection of prion shedding in saliva and urine throughout the course of CWD disease in deer by RT-QuIC.

DETAILED DESCRIPTION OF THE PREFERRED EMBODIMENT

Figure 1:
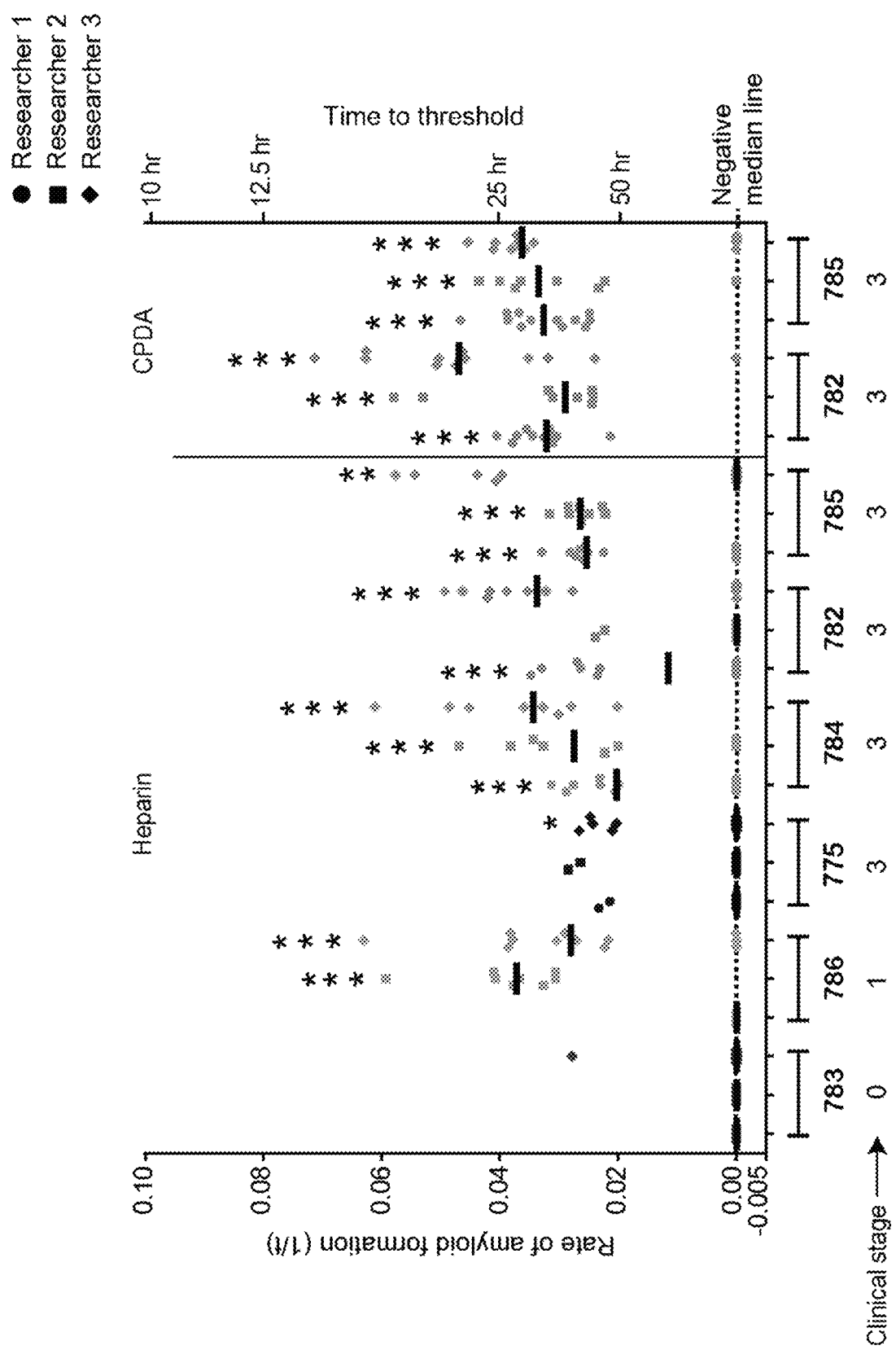
FIG. 1 is a graph showing prionemia detection in buffy coat cells by lipase iron-oxide bead RT-QuIC (LIQ42). Amyloid seeding activity was detected in $5 \times 10^5$ buffy coat cells from four of six deer tested (1 g CWD+ brain inoculated) using lipase iron-oxide bead RT-QuIC performed at 42° C. Positive deer were in CWD clinical stages 1 and 3. Experiments were performed by three researchers (circle, square, diamond) on blinded samples (8-12 replicates/researcher/deer; medians shown with black line). n=254 replicates from n=24 sham-inoculated negative control deer are represented by the negative median line. Statistical significance between infected and negative control deer is indicated with asterisks (p=0.0159-0.0001).

Development of noninvasive, rapid and robust assays to detect prion infections throughout the course of disease are continuously being sought. Currently, the definitive diagnosis for prion diseases is by post-mortem examination of brain and lymphoid tissues for the presence of prion deposition ($PrP^{Sc}$) by immunohistochemistry, the gold standard for prion detection. This process is expensive, time consuming and is most efficient in detecting high vs low prion burdens. Bodily fluids of prion-infected hosts harbor infectivity. In vitro amplification assays can recognize accumulated amyloid formation associated with prion infections. Detecting the presence of low concentrations of the prion agent in biological tissues and fluids mandates modifications to these assays. CWD pathogenesis studies were capitalized upon to refine in vitro prion amplification methods to detect blood borne prions. The present invention provides in vitro prion detection in blood components as demonstrated in cervids orally-inoculated with CWD+ doses ranging from high (1 g) to low (300 ng) quantities of brain and more biologically relevant milieu (saliva).

The ability to detect prions is demonstrated in as few as $5 \times 10^5$ buffy coat cells by lipase-iron oxide bead-RT-QuIC performed at 42° C. (LIQ42) in 79% of CWD-biopsy positive WTD, which increased to 100% when LIQ was performed at 55° C. (LIQ55). RT-QuIC assessment of PMCA (PQ) round 5 product revealed hematogenous prions in 92% of the WTD.

The in vitro detection of hematogenous prions has been elusive as reliable detection is fraught with challenges. The use of amplification assays, PMCA and RT-QuIC, have steadily gained prowess in permitting detection of prions present in blood components of experimental and free-range naturally-exposed cervids, scrapie-infected sheep and humans infected with CID. Pre-amplification methods designed to concentrate prions or remove inhibitors associated with bodily fluids can be used prior to amplification by RT-QuIC and PMCA. Pre-amplification methods can help to reveal the presence of amyloid seeding activity in biological fluids harvested from prion-infected hosts.

It is shown herein that increasing the temperature at which LIQ is performed from 42° C. to 55° C., and combined use of PMCA and RT-QuIC (PQ) provide enhanced sensitivity and detection confirmation of prionemia in CWD-infected WTD. The use of higher temperatures for the RT-QuIC assay results in enhanced amyloid signal-to-noise ratios. Combined use of RT-QuIC and PMCA is a powerful platform to amplify minute quantities of amyloid present in tissues of CWD-infected WTD. By incorporating RT-QuIC readout of PMCA product we demonstrate the presence of hematogenous prions in lymphoid biopsy positive, yet LIQ42 negative cervids, supporting the combined assay use to confirm the presence of low circulating CWD prionemia.

The number of buffy coat cells required for LIQ and PQ detection of hematogenous prions is shown herein to represent that present in approximately 0.5-1 ml of WTD blood. Collection of 10-15 ml whole blood is sufficient to harvest adequate numbers of cells to perform either assay, making longitudinal assessment over the course of disease feasible. Adequate leukocyte numbers are present in similar volumes of human, sheep, and cattle whole blood.

Of particular interest is the detection of blood-borne prions in cervids dosed with progressively lower concentrations of CWD; 1 g, 1 mg or 300 ng. It is suspected that prion exposures in nature are quite low [Zabel M, Ortega A. The Ecology of Prions. Microbiol Mol Biol Rev. 2017; 81(3)]. Studies to define minimum infectious dose in native species have been undertaken. In sheep scrapie, sufficient infectivity to initiate disease has been described after intravenous inoculation of $10^5$ white blood cells or 100 μl whole blood [Douet J Y, Lacroux C, Litaise C, Lugan S, Corbiere F, Arnold M, et al. Mononucleated Blood Cell Populations Display Different Abilities To Transmit Prion Disease by the Transfusion Route. J Virol. 2016; 90(7):3439-45]. Our own studies in WTD demonstrate that oral doses of 1 mg and 300 ng brain or 300 ng saliva equivalent contain sufficient infectivity to initiate CWD infection [Denkers N D, Hoover C E, Davenport K A, Henderson D M, McNulty E E, Nalls A V, Mathiason C K, Hoover E A. Very low oral exposure to prions of brain or saliva origin transmits chronic wasting disease. PLoS One 2020 Aug. 20; 15(8):e0237410. doi: 10.1371/journal.pone.0237410. PMID: 32817706; Cooper S K, Hoover C E, Henderson D M, Haley N J, Mathiason C K, Hoover E A. Detection of CWD in cervids by RT-QuIC assay of third eyelids. PLoS One. 2019; 14(8):e0221654]. These doses are 3-9 logs lower than previous experimental exposures, supporting evidence that low dose exposure initiates infection. Thus, the generation of in vitro methods with capacity to detect low level exposure is paramount.

Cervids in the pre-clinical phase of disease carry and shed infectivity [Haley N J, Seelig D M, Zabel M D, Telling G C, Hoover E A. Detection of CWD prions in urine and saliva of deer by transgenic mouse bioassay. PLoS One. 2009; 4(3):e4848; Miller M W, Williams E S, Hobbs N T, Wolfe L L. Environmental sources of prion transmission in mule deer. Emerg Infect Dis. 2004; 10(6):1003-6]. During the protracted pre-clinical phase of disease CWD burden in tissues and shed components are low and intermittent [Henderson D M, Denkers N D, Hoover C E, Garbino N, Mathiason C K, Hoover E A. Longitudinal Detection of Prion Shedding in Saliva and Urine by Chronic Wasting Disease-Infected Deer by Real-Time Quaking-Induced Conversion. J Virol. 2015; 89(18):9338-47; Haley N J, Mathiason C K, Carver S, Zabel M, Telling G C, Hoover E A. Detection of chronic wasting disease prions in salivary, urinary, and intestinal tissues of deer: potential mechanisms of prion shedding and transmission. J Virol. 2011; 85(13): 6309-18]. Further evidence is provided herein that prionemia can be identified at all stages of disease course (Stages 0-3). Circulating prion burdens in blood are estimated to be in the 13-260 fg ml$^{-1}$-0.5 pg ml$^{-1}$ range [Chen B, Morales R, Barria M A, Soto C. Estimating prion concentration in fluids and tissues by quantitative PMCA. Nat Methods. 2010; 7(7):519-20] and may be intermittent across the longitudinal course of disease [Lacroux C, Comoy E, Moudjou M, Perret-Liaudet A, Lugan S, Litaise C, et al. Preclinical detection of variant CJD and BSE prions in blood. PLoS Pathog. 2014; 10(6):e1004202; Kramm C, Pritzkow S, Lyon A, Nichols T, Morales R, Soto C. Detection of Prions in Blood of Cervids at the Asymptomatic Stage of Chronic Wasting Disease. Sci Rep. 2017; 7(1):17241].

CWD continues its geographical, host range and strain expansion across North America, Korea, and Scandinavia. Furthermore, new CWD strains have been reported in cervid populations. It is unknown if new CWD strains are more or less infectious to cervid populations. Of considerable concern is whether new strains have increased propensity to cross species barriers to humans and other species sympatric with CWD-infected cervids. One in 36 Americans (roughly 9 million) hunt North American big game. Estimates show that 7,000 to 15,000 CWD-positive cervids are consumed per year and that this number increases by ~20% every year. CWD-infected yet conventional test negative (pre-clinical) cervids are prevalent in native populations [Selariu A, Powers J G, Nalls A, Brandhuber M, Mayfield A, Fullaway S, et al. In utero transmission and tissue distribution of chronic wasting disease-associated prions in free-ranging Rocky Mountain elk. J Gen Virol. 2015; Monello R J, Powers J G, Hobbs N T, Spraker T R, O'Rourke K I, Wild M A. Efficacy of antemortem rectal biopsies to diagnose and estimate prevalence of chronic wasting disease in free-ranging cow elk (*Cervus elaphus nelsoni*). J Wildl Dis. 2013; 49(2):270-8]. Venison is shared among family and friends and is the mainstay protein for many indigenous populations. Although fewer numbers of people consume product from a potentially CWD-infected carcass, this results in higher consumption per person. Bioassay has confirmed the presence of CWD infectivity in cervid muscle [Pattison I H M G. Distribution of the Scrapie agent in the Tissues of Experimentally inoculated goats. J Comp Pathol. 1962; 76:233-44; Angers R C, Browning S R, Seward T S, Sigurdson C J, Miller M W, Hoover E A, et al. Prions in skeletal muscles of deer with chronic wasting disease. Science. 2006; 311(5764):1117]. While no human cases of CWD have been detected, it was thought BSE would not become a human pathogen several years before vCJD was discovered [Diack A B, Will R G, Manson J C. Public health risks from pre-clinical variant CJD. PLoS Pathog. 2017; 13(11):e1006642; Houston F, Andreoletti O. Animal prion diseases: the risks to human health. Brain Pathol. 2019; 29(2):248-62; Hodgson E. BSE. An unlikely zoonosis. Occup Health (Lond). 1990; 42(9):265-6; Will R G. The spongiform encephalopathies. J Neurol Neurosurg Psychiatry. 1991; 54(9):761-3].

The methodologies taught herein provide a path to assess prion pathogenesis throughout the disease process that will be instrumental in the development of vaccines, therapeutics and management practices to mitigate CWD, and by extension, other prion and protein misfolding disorders (e.g. CID, CWD, BSE, TME, scrapie, Alzheimer's Disease, Parkinson's Disease, Amyotrophic Lateral Sclerosis, Chronic Traumatic Encephalopathy, Fronto-Temporal Dementia, and System Atrophy).

Example 1—Materials and Methods

White-tailed deer: White-tailed deer (WTD) that were part of previous transmission studies and were of known CWD status at Colorado State University (CSU) [Goni F, Mathiason C K, Yim L, Wong K, Hayes-Klug J, Nalls A, et al. Mucosal immunization with an attenuated *Salmonella* vaccine partially protects white-tailed deer from chronic wasting disease. Vaccine. 2015; 33(5):726-33; Cooper S K, Hoover C E, Henderson D M, Haley N J, Mathiason C K, Hoover E A. Detection of CWD in cervids by RT-QuIC assay of third eyelids. PLoS One. 2019; 14(8):e0221654] were used for this work. WTD fawns were provided by the Warnell School of Forestry and Natural Resources, University of Georgia, Athens (UGA)—a region in which CWD has not been detected. The fawns were hand-raised and human- and indoor-adapted before being transported directly to the CSU CWD indoor isolation research facility without contact with the native Colorado environment. All deer were housed, handled, anesthetized, and euthanized as per CSU International Animal Care and Use Committee (IACUC) approved protocols 11-2622A, 12-3773A, 18-8396A, and 18-7969A.

CWD clinical stage scoring system: All deer were assessed for CWD status at study termination. The scoring of stages is as follows: Stage 0: Normal behavior and physiological homeostasis. Stage 1: Animal shows a subtle behavioral change. Diurnal rhythms and patterns of sleeping, feeding and activity may be altered. This is only obvious to a caregiver when an individual from a group fails to respond to the presence of a caregiver. When aroused, the affected animal may show a decreased level of investigatory behavior and in some cases are hyper-reactive to stimuli. Stage 2: In addition to Stage 1 behavior there is a mild but observable neurological deficit. This is most commonly seen as mild ataxia in the hind-quarters, but may include the front legs and head tossing. The animal is fully mobile and continues to interact. Stage 3: Early: In addition to Stage 2 behavior the animal is beginning to show early signs of deterioration (weight loss/altered gait) and continued progression of ataxia. Loss of coat condition becomes more obvious in association with a loss of grooming behavior. Appetite and ability to eat and drink remain intact. Late: Gait abnormalities become pronounced. Locomotion varies from normal to moderately ataxic. There are obvious signs of muscle wasting even though appetite and ability to eat and drink remain intact, and in some cases increase.

White-tailed deer cohorts: A total of 16 deer were used for this work (summarized in Table 1). CWD status was determined by immunohistochemistry of lymphoid tissues harvested from each WTD over the course of the study and at termination as well as behavior scoring. All deer were lymphoid biopsy positive at termination, but varied in clinical status. Deer received the following inoculum [Goni F, Mathiason C K, Yim L, Wong K, Hayes-Klug J, Nalls A, et al. Mucosal immunization with an attenuated *Salmonella* vaccine partially protects white-tailed deer from chronic wasting disease. Vaccine. 2015; 33(5):726-33; Cooper S K, Hoover C E, Henderson D M, Haley N J, Mathiason C K, Hoover E A. Detection of CWD in cervids by RT-QuIC assay of third eyelids. PLoS One. 2019; 14(8):e0221654]; 1 g CWD+ brain homogenate (CBP6): n=6 deer (#775, #782, #783, #784, #785, #786) were inoculated per os (PO) and were sacrificed between 16- and 32-months post inoculation (mpi). The deer were in CWD clinical Stage 0-1 (#775, #783, #786) or Late 3 (#782, #784, #785) when terminated. 1 mg CWD+ brain homogenate (CBP6): n=3 deer (#1308, #1305, and #1310) were inoculated with 1 mg PO of CWD-positive deer brain and were sacrificed at 18, 28 and 28 mpi respectively. The deer were in CWD clinical Stage 0 (#1305, 1310) or Late 3 (#1308) at the time of termination. 300 ng CWD+ brain homogenate (CBP6): An additional n=3 deer (#1303, #1316, and #1307) were dosed PO with a total of 300 ng CBP6 in three weekly doses of 100 ng/each, and were sacrificed at 22, 23, and 28 mpi respectively. The deer were in CWD clinical Stage 0 (#1307), 2 (#1316) or Late 3 (#1303). 300 ng CWD+ saliva equivalent: n=2 deer (#1313 and #1309) received a total of 30 ml saliva (containing 300 ng brain (CBP6) equivalent seeding activity in RT-QuIC)) in weekly PO doses of 10 ml and were sacrificed at 25 and 28 mpi respectively. The deer were in CWD clinical Stage 2 (#1309) and Early 3 (#1313). Negative controls: n=2 deer (#502 and #1444) served as sham-inoculated negative controls that remained in clinical Stage 0. CWD status was determined by immunohistochemistry of lymphoid tissues harvested from each WTD over the course of the study and at termination as well as behavior scoring.

Whole blood collection and buffy coat harvest: Whole blood was collected in heparin (200 units ml$^{-1}$) and CPDA-1 (0.2 ml CPDA ml$^{-1}$ blood) from each WTD at study termination (Table 1). Anticoagulant buffered whole blood samples (40 ml) were centrifuged at 1600 rpm for 15 min at 4° C. Buffy coat cells, including leukocytes and platelets, were harvested from the discreet band present post centrifugation. Cells were placed in 35 ml lysing buffer and washed 2 times with phosphate buffered saline (PBS: 20 mM NaPO$_4$, 150 mM NaCl, pH 7.4), centrifugation between and after washes. Cells were counted by the Countess (Invitrogen) and adjusted to 1×10$^7$ cells and stored at −80° C. as a dry pellet.

Lipase and iron oxide bead (IOB) treatment: After thawing, the samples were resuspended in a 1×10$^7$ cells ml$^{-1}$ concentration in PBS and homogenized in an Omni Bead Ruptor (Power 5, two 30 sec shakes with a mid-10 sec break). A further dilution of 1:20 (50 µl sample+950 µl PBS) was made to adjust final cell numbers to 5×10$^5$ cells ml$^{-1}$ PBS and was placed in a 1.7 ml microfuge tube containing 5 µl (4.5 units) lipase B (Lipase B *Candida antarctica*, recombinant from *Aspergillus oryzae*; Sigma-Aldrich), 8 µl (0.4 units) lipase C (Phospholipase C from *Clostridium perfringens* (*welchii*)) with 1 h incubation at 37° C. in a thermomixer at 1400 rpm (Eppendorf). Following lipase treatment, the samples were added to 2 µl IOB (49 mg ml$^{-1}$, ~9 µm; Bangs Laboratories, Indiana BioMag superparamagnetic iron oxide lot #10250) in a 1.7 ml tube. Samples were mixed end-over-end at room temperature for 30 min. Each sample was placed in a magnetic tray to recover the IOB fraction (magnetic particle separator, Pure Biotech, New Jersey). IOB were resuspended in 10 µl 0.1% SDS (sodium dodecyl sulfate, Sigma-Aldrich).

rPrP production: Truncated Syrian hamster (SH) PrP$^C$ for RT-QuIC was expressed [Wilham J M, Orru C D, Bessen R A, Atarashi R, Sano K, Race B, et al. Rapid end-point quantitation of prion seeding activity with sensitivity comparable to bioassays. PLoS Pathog. 2010; 6(12):e1001217; Henderson D M, Manca M, Haley N J, Denkers N D, Nalls A V, Mathiason C K, et al. Rapid antemortem detection of CWD prions in deer saliva. PLoS One. 2013; 8(9):e74377]. Briefly, we added BL21 cells containing the sequence for the expression of amino acids 90 to 231 of SH PrP$^C$ to 5 ml LB medium, grew the cultures overnight, and then added the bacteria to 1 L LB medium with autoinduction reagents (final concentrations, 0.5 M (NH$_4$)$_2$SO$_4$, 1 M KH$_2$PO$_4$, 1 M Na$_2$HPO$_4$, 0.5% glycerol, 0.05% glucose, 0.2% α-lactose, and 0.001 M MgSO$_4$). When the optical density at 600 nm (OD600) reached approximately 1.7, we lysed the cells and purified the inclusion bodies according to the manufacturer's protocol with BugBuster and Lysonase (EMD-Millipore). To purify recombinant PrP (rPrP), we solubilized the inclusion bodies in 8 M guanidine hydrochloride (GdnHCl) and 100 mM Na$_2$HPO$_4$ at room temperature overnight in an end-over-end rotator. We mixed the denatured rPrP slurry with Superflow nickel resin (Qiagen), refolded the rPrP on the column, and eluted it.

RT-QuIC reactions: Each sample was plated 3 µl/well in quadruplicate in a 96 well plate (Greiner Bio-One optical bottom plate) containing 98 µl reaction mix (320 mM NaCl, 1.0 mM EDTA, 10 µM Thioflavin T (Sigma)) and placed in a FLUOstar Omega plate reader with 700 rpm double-orbital shaking for 50 h. The FLUOstar Omega reader collected fluorescence readings at 15 min intervals. CBP6 (CWD-positive) and 123 (CWD-negative) brain material were utilized as plate and assay controls. Samples were considered positive if they crossed a threshold (5 SD above the mean of the initial 5 readings). The inverse of the time when the reaction reached the threshold (1/time to threshold) was then used to determine the amyloid formation rate. Statistical analyses were run in Prism v6 (GraphPad Software, La Jolla, Calif.). A Mann-Whitney test was used to generate statistical significance (p-values <0.05 were considered significant) by comparing the sample rates to the rates of known negative control tissues [McNulty E, Nalls A V, Mellentine S, Hughes E, Pulscher L, Hoover E A, et al. Comparison of conventional, amplification and bio-assay detection methods for a chronic wasting disease inoculum pool. PLoS One. 2019; 14(5):e0216621].

Normal brain homogenate (NBH) for PMCA: Brains from cervidized transgenic mice were used for the PrP$^C$ substrate for PMCA prion conversion, prepared as follows: naïve Tg(CerPrP) 5037 mice <4 months of age were euthanized by CO$_2$ inhalation and perfused with 35 ml of 5 mM ethylenediaminetetraacetic acid tetrasodium salt (EDTA) in PBS via intracardiac catheterization. The brain was removed and flash frozen using liquid nitrogen. Brain homogenate was then prepared at a 10% (w/v) solution in PMCA buffer (1% Triton-X 100 (v/v), 5 mM EDTA, and 150 mM NaCl) with the addition of Complete Protease Inhibitors (Roche Pharmaceuticals, Indianapolis, Ind.) in a homogenizer (Omni Bead Ruptor). Homogenates were then centrifuged for 1 min at 3000 rpm to remove bulk brain material, and the supernatant frozen in single-experiment aliquots at −80° C. in a prion-free room until use in PMCA.

PMCA reactions: Dilutions of buffy coat samples were spun down and reconstituted in 10 μl PBS, sonicated for 60 sec, and spiked into 90 μl 10% NBH (w/v) in PCR microfuge tubes in single. Tubes were sonicated (30 sec every 29.5 min) for the first 72 h, then for 24 h rounds thereafter. After each round, 20 μl material was transferred into 50 μl fresh NBH and subjected to the next round for a total of 5 rounds (72 h first, then 4-24 h rounds). After 5 rounds, a 1:100 dilution of sample was analyzed by RT-QuIC.

Western blot: Brain tissue from CBP6 (CWD-positive) and 123 (CWD-negative) deer was prepared as a 10% (w/v) homogenates in PBS and utilized as western blot controls. Round 5 PMCA buffy coat cell dilutions (ranging from $1\times10^6$-$3.125\times10^4$) and brain controls were mixed with proteinase K (PK; Invitrogen) at 50 μg/mL, incubated at 42° C. for 40 min. Samples were mixed with reducing agent (10×)-lithium dodecyl sulfate (LDS) sample buffer (4×) (Invitrogen) at a concentration of 1×, heated at 95° C. for 5 min and separated on NuPAGE 12% Bis-Tris gel at 125V for 1.5 h. Protein was transferred to a polyvinylidene fluoride (PVDF) membrane at 80 V for 1 h in transfer buffer (0.025 M Trizma base, 0.2 M glycine, 20% methanol, pH 8.3). The membrane was then incubated with 5% nonfat milk in 1×Tris-buffered saline (TBS) with 0.1% Tween 20 (TBST) for 3 min and then for 12 min with BAR224-HRP (0.2 μg/ml final concentration; Cayman Chemical) diluted in TBST, followed by a 30 min wash with TBST. The membrane was then developed with ECL Plus Western blotting detection reagents (Pierce) and viewed on a Luminescent Image Analyzer LAS-4000 (Fujifilm).

Example 2—Prionemia Detected in $5\times10^5$ Buffy Coat Blood Cells by Lipase Real Time Quaking Induced Conversion (LIQ) Assay Amplification assays can be used to assess blood products harvested from CWD-exposed and infected cervids for the presence of amyloid associated with prion disease. The ability of amplification assays to detect CWD prions in buffy coat blood cells harvested from cervids receiving a more biologically relevant dose (300 ng) and milieu (saliva) is demonstrated herein.

Amyloid seeding activity, referred to as "prionemia" herein, was detected in $5\times10^5$ buffy coat blood cells harvested from four of six (4/6) white-tailed deer (WTD) orally-dosed with 1 g CWD+ brain homogenate (#786, #784, #782, #785) using a modified RT-QuIC assay; lipase iron-oxide bead RT-QuIC performed at 42° C. (LIQ42) (FIG. 1, Table 1). These results were confirmed by three independent researchers with blinded samples. Of the four 1 g LIQ+ WTD, three (#784, #782, #785) were in late Stage 3 clinical disease, and the one remaining deer (#786) was in clinical Stage 0-1 (Table 1). LIQ detection was equally efficient for blood collected into heparin or CPDA anticoagulants, however detection was more robust in CPDA samples (FIG. 1). Therefore, subsequent analyses were performed with CPDA anticoagulated blood.

Figure 2:
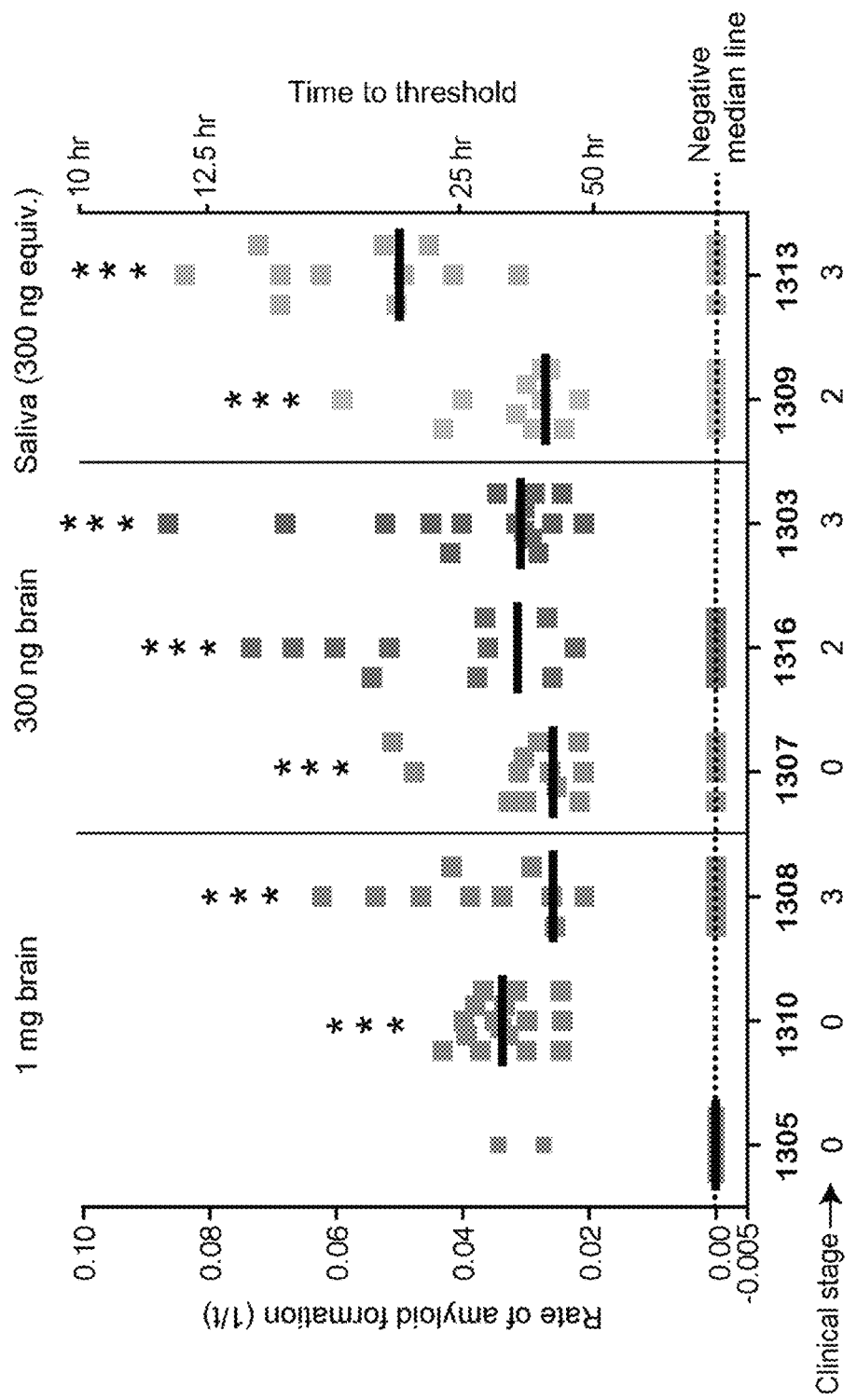
FIG. 2 is a graph showing prionemia detection in buffy coat cells from pre-clinical and clinical deer inoculated with low doses of CWD+ brain and saliva by lipase iron-oxide bead RT-QuIC (LIQ42). Amyloid seeding activity was detected in $5 \times 10^5$ buffy coat cells from seven of eight deer tested (inoculated with 1 mg or 300 ng CWD+ brain or 300 ng CWD+ saliva equivalent) using lipase iron-oxide bead RT-QuIC performed at 42° C. Positive deer were pre-clinical or in CWD clinical stages 2 and 3. Black lines represent the median of 16 replicates per deer. n=64 replicates from n=2 sham-inoculated negative control deer are represented by the negative median line. Statistical significance between infected and negative control deer is indicated with asterisks (p=0.0002-0.0001).

Example 3—LIQ Detection of Prionemia in Cervids Receiving Low Doses (1 mg or 300 ng) of CWD We further assessed LIQ42's ability to detect amyloid seeding activity in buffy coat blood cells harvested from WTD orally dosed with 1 mg or 300 ng CWD+ brain homogenate or 300 ng CWD+ saliva equivalent (FIG. 2, Table 1). We detected amyloid seeding activity in two of three (2/3) 1 mg (#1310, #1308) and three of three (3/3) 300 ng CWD+ brain-dosed WTD (#1307, #1316, #1303), and two of two (2/2) 300 ng CWD+ saliva equivalent-dosed WTD (#1309, #1313). Clinical disease status ranged from Stage 0-Late 3 (Table 1). LIQ detected hematogenous prions in two of three (2/3) WTD in pre-clinical Stage 0, and five of five (5/5) WTD in clinical Stage 2-Late 3. No preferential detection was observed based on the source or concentration of inoculum each WTD received (FIG. 2, Table 1).

Figure 3:
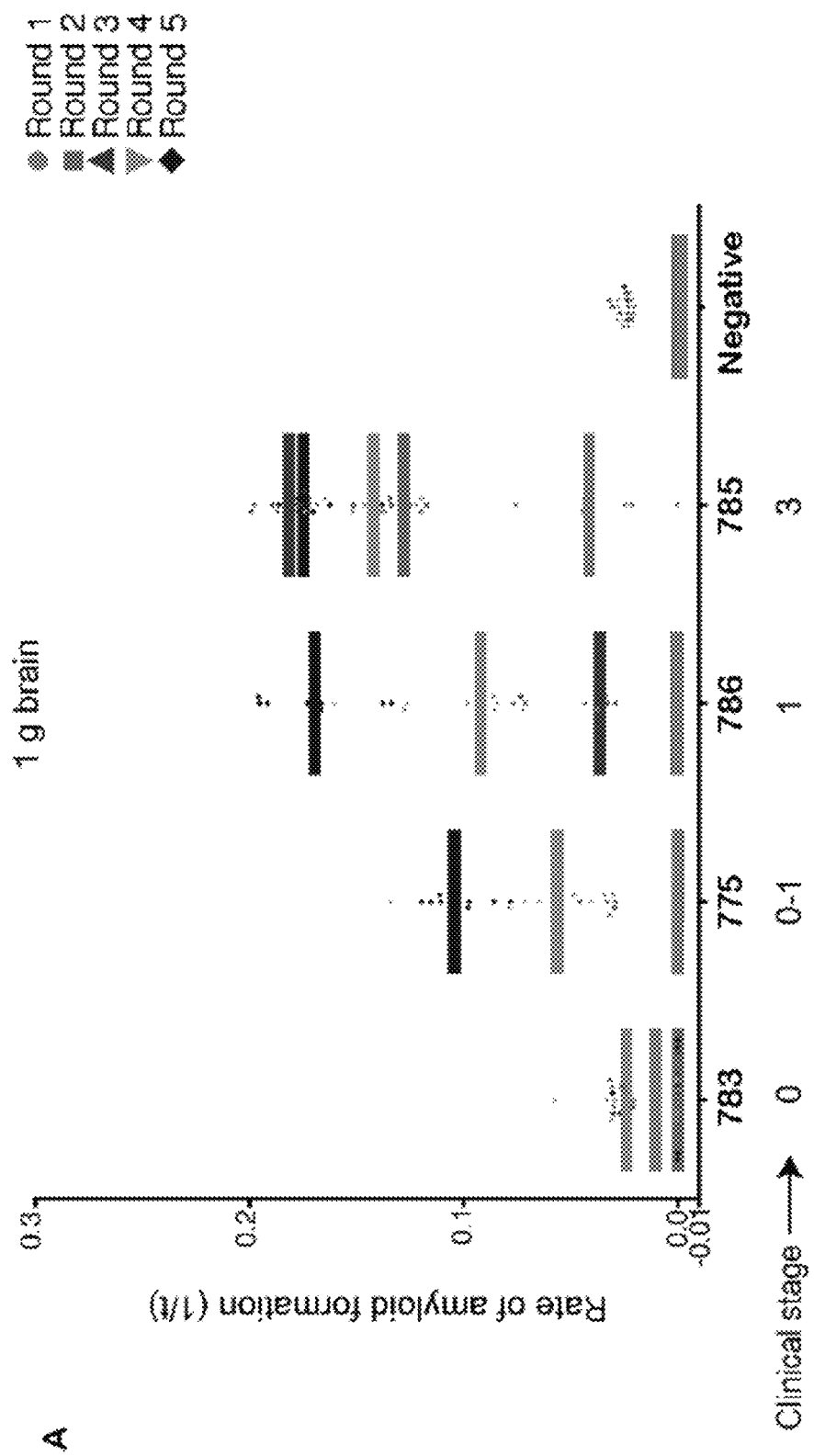
FIG. 3 is a pair of graphs (A and B) showing that RT-QuIC combined with PMCA (PQ) confirms prionemia found in $5 \times 10^5$ buffy coat cells and enhanced detection in CWD-infected WTD. (A) Amyloid seeding activity was confirmed in $5 \times 10^5$ buffy coat cells from three of four deer tested (inoculated with 1 g CWD+ brain) by RT-QuIC combined with PMCA (PQ) within 4 rounds. (B) PQ confirmed prionemia in deer inoculated with low doses of CWD (1 mg or 300 ng CWD+ brain or 300 ng CWD+ saliva equivalent), detecting seeding activity in all eight deer. Lines represent the median of 8 replicates/round/deer and different shapes represent replicates of different rounds. Negative replicates from 2 sham-inoculated control deer are shown. Statistical significance between infected and negative control deer is listed in Table 2.
Figure 7:
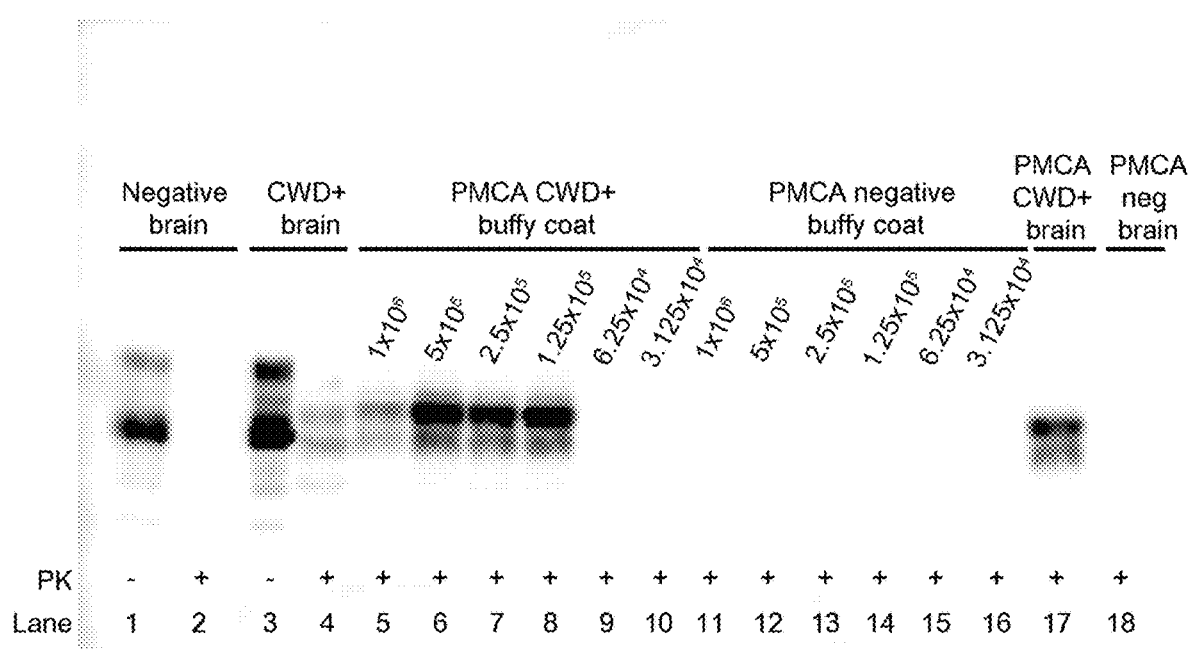
FIG. 7 is an image showing that Western blot confirms presence of PK resistant material in buffy coat cells by PMCA. Detection of PrP$^{Sc}$ is shown in PMCA products initiated with buffy coat cell amounts ranging from $1 \times 10^6$ cells down to $1.25 \times 10^5$ cells (5 rounds PMCA; initiating seed=10 µl) in lanes 5-8. No PrP$^{Sc}$ was found in lanes 9-10, products initiated with $6.25 \times 10^4$ and $3.125 \times 10^4$ cells. PMCA products initiated with $1 \times 10^6$ to $3.125 \times 10^4$ cells collected from a negative deer remained negative (lanes 11-16). CWD+ and CWD-negative amplified brain controls are in lanes 17 and 18. Complete PK digestion of PrP$^C$ is shown in unamplified (lane 2) and sPMCA amplified negative deer brain (5 rounds; lane 18).

Example 4—RT-QuIC Combined with PMCA (PQ) Confirms Prionemia in $5\times10^5$ Buffy Coat Blood Cells and Enhances Detection Sensitivity To serve as a confirmatory test of LIQ results, we first assessed $5\times10^5$ buffy coat blood cells harvested from WTD white-tailed deer (WTD) orally-dosed with 1 g CWD+ brain homogenate in clinical Stage 0-3 by RT-QuIC readout of PMCA product (PQ) (rounds 1-5), and detected amyloid seeding activity in three of four (3/4) deer (#775, #786, #785) within 4 rounds (FIG. 3A). To further determine if PQ had sufficient sensitivity to detect hematogenous prions in WTD receiving lower doses of CWD and during earlier stages of disease, we assessed $5\times10^5$ buffy coat blood cells harvested from WTD in clinical Stage 0-3 that had been orally dosed with 1 mg or 300 ng CWD+ brain or 300 ng CWD+ saliva equivalent and detected amyloid seeding activity in eight of eight (8/8) deer (#1305, #1310, #1308, #1307, #1316, #1303, #1309, #1313) after 1-5 rounds (FIG. 3B). In particular, improved detection sensitivity is seen when PMCA product is read by RT-QuIC vs by western blot. (See e.g. FIG. 7)

Figure 4:
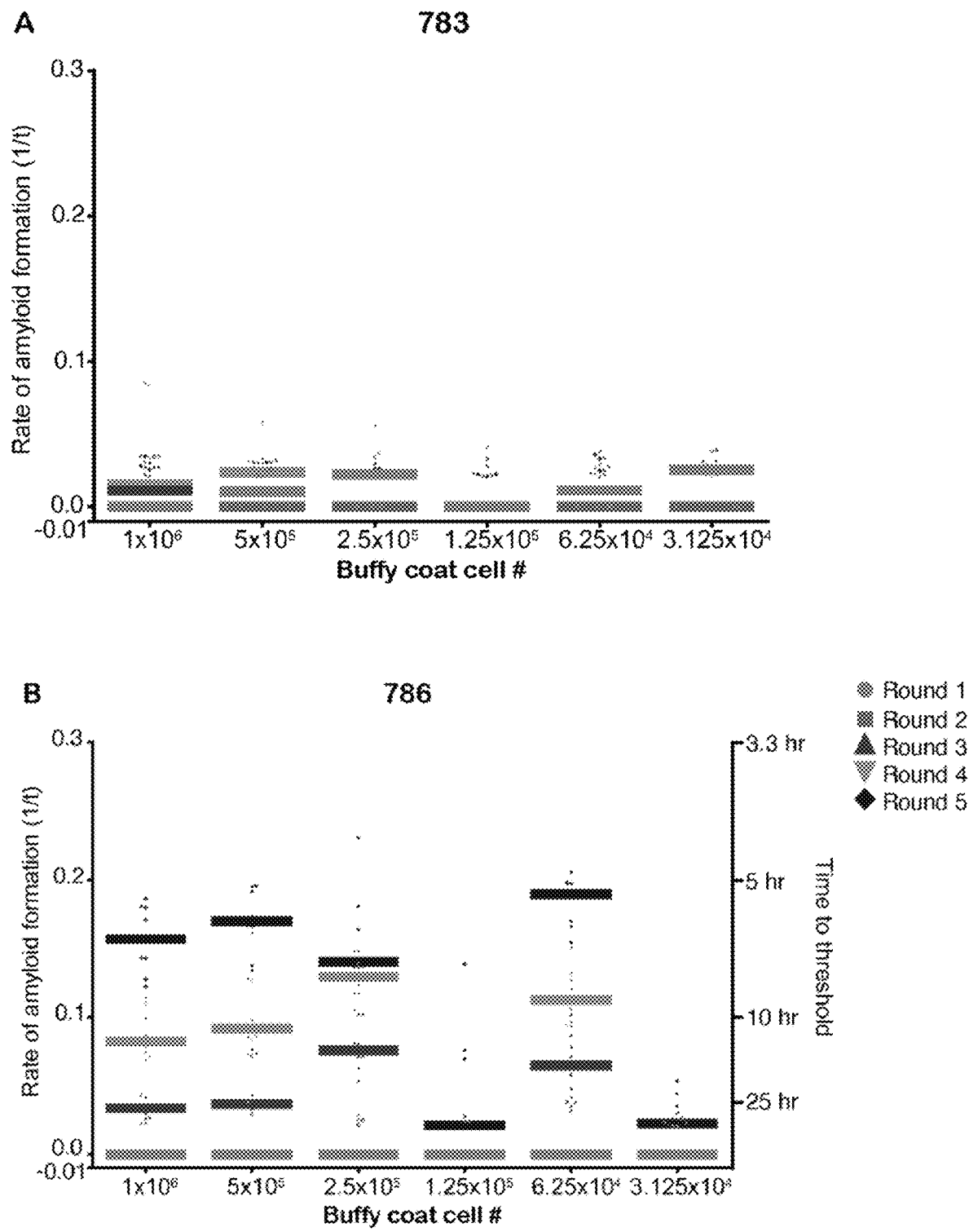
FIG. 4 is a set of five (5) graphs (A-E) showing PQ detection of prionemia in as few as $3.125 \times 10^4$ buffy coat cells from deer inoculated with 1 g brain. (B-D) Amyloid seeding activity was detected in $1 \times 10^6$-$3.125 \times 10^4$ buffy coat cells from three CWD+ clinical deer tested by PQ after 1-5 rounds, but was not detected in the pre-clinical deer (A). Lines represent the median of 8 replicates/round/deer and different shapes represent replicates of different rounds. (E) Negative replicates from 2 sham-inoculated control deer are shown. Statistical significance between infected and negative control deer is listed in Table 2.

Example 5—PQ Detection of Prionemia in as Few as $3.125\times10^4$ Buffy Coat Blood Cells By incorporating PQ we were able to detect amyloid seeding activity in as few as $3.125\times10^4$ buffy coat cells harvested from three of the four (#775, #786, #785; Stage 0-3) deer dosed with 1 gr CWD+ brain after 1-5 rounds of PMCA (FIG. 4A-D). Similar PQ reactions of buffy coat cells ($1\times10^6$-$3.125\times10^4$) harvested from sham-inoculated negative controls (#502, #1444) were void of amyloid seeding activity (FIG. 4E).

Figure 5:
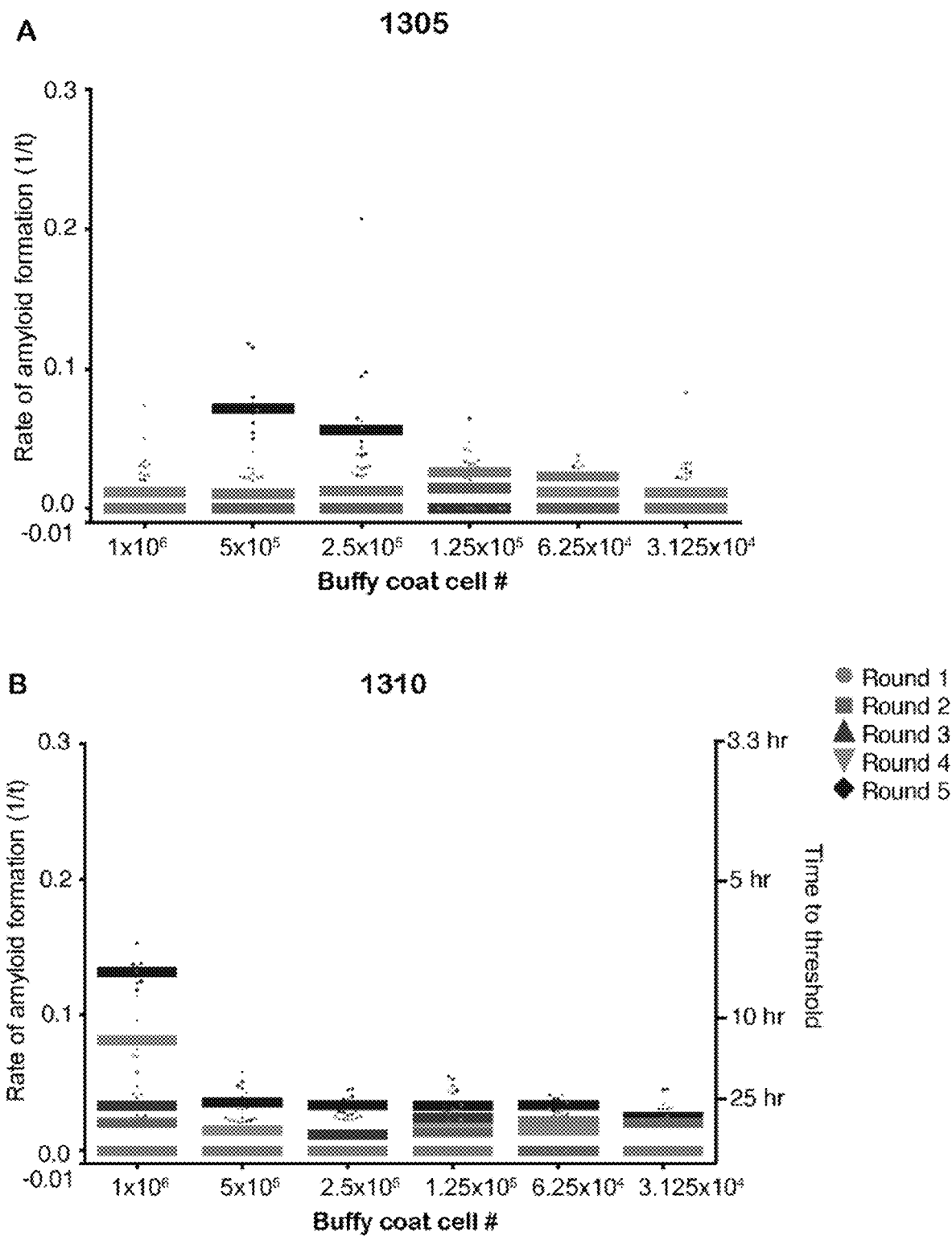
FIG. 5 is a set of three (3) graphs (A-C) showing PQ detection of prionemia in as few as $6.25 \times 10^4$ buffy coat cells from deer inoculated with 1 mg CWD+ brain. (A-C) Amyloid seeding activity was detected in $6.25 \times 10^4$ buffy coat cells from one CWD+ clinical deer using PQ after 1 round of PMCA, and in $1 \times 10^6$-$2.5 \times 10^5$ buffy coat cells from pre-clinical deer after 1-5 rounds. Lines represent the median of 8 replicates/round/deer and different shapes represent replicates of different rounds. Statistical significance between infected and negative control deer (FIG. 4E) is listed in Table 2.
Figure 6:
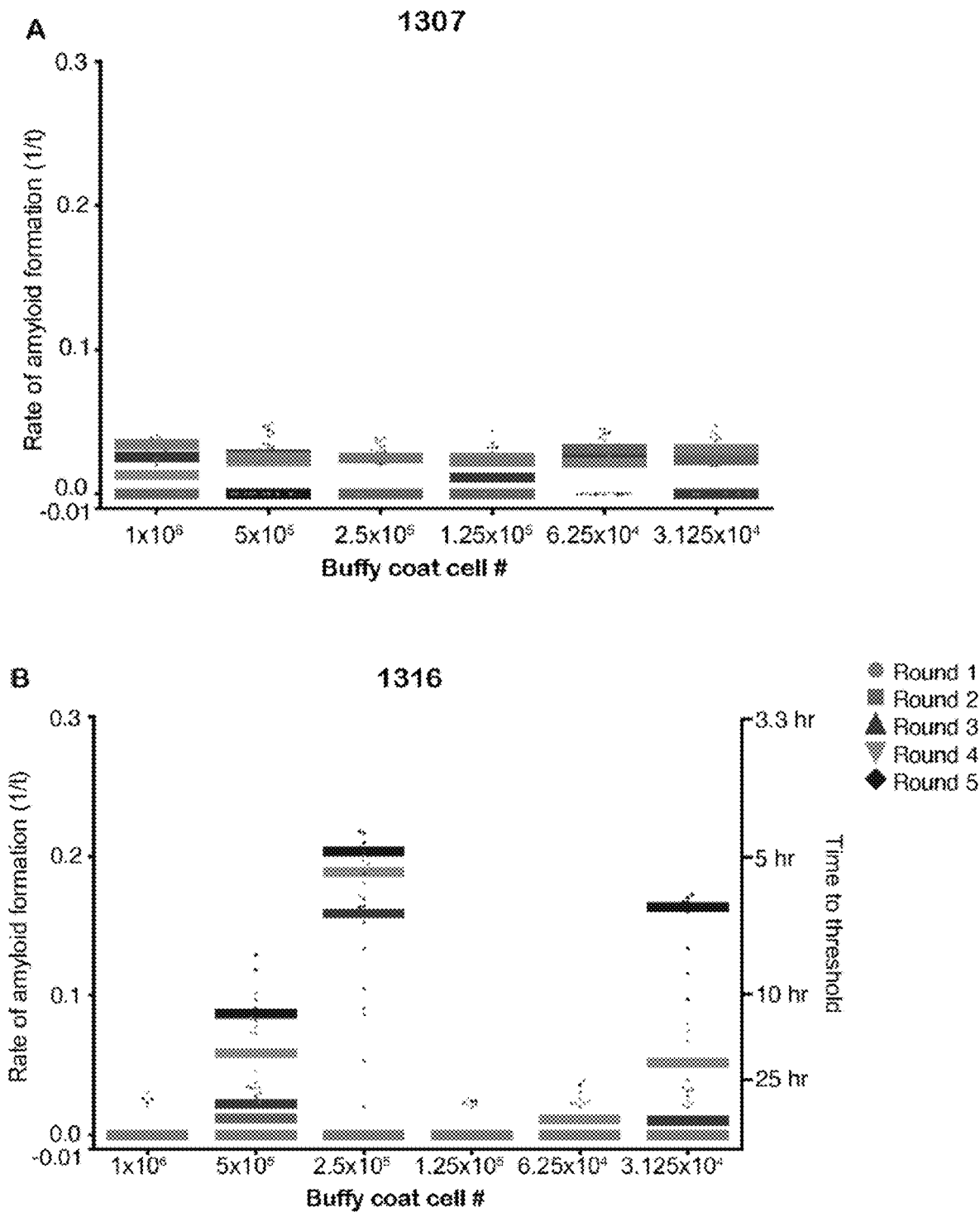
FIG. 6 is a set of five (5) graphs (A-E) showing PQ detection of prionemia in as few as $3.125 \times 10^4$-$6.25 \times 10^4$ buffy coat cells from deer inoculated with 300 ng CWD+ brain or 300 ng CWD+ saliva equivalent. (A-C) Amyloid seeding activity was detected in as few as $3.125 \times 10^4$ buffy coat cells after 1-5 rounds of PMCA in all three deer that received 300 ng CWD+ brain and in as few as $6.25 \times 10^4$ buffy coat cells from both deer dosed with 300 ng CWD+ saliva equivalent after 5 rounds of PMCA. Lines represent the median of 8 replicates/round/deer and different shapes represent replicates of different rounds. Statistical significance between infected and negative control deer (FIG. 4E) is listed in Table 2.

PQ had sufficient sensitivity to detect hematogenous prions in WTD receiving lower oral doses of CWD (1 mg or 300 ng brain or 300 ng saliva equivalent; Stage 0-3). PQ revealed amyloid seeding activity in as few as $6.25\times10^4$ (Stage 3) and $2.5\times10^5$ (Stage 0) buffy coat cells harvested from all three WTD orally dosed with 1 mg CWD+ brain (#1305, #1310, #1308) after 1-5 rounds of PMCA (FIG. 5, Tables 1 and 2). PQ was able to detect amyloid seeding activity in as few as $3.125\times10^4$ buffy coat cells after 1-5 rounds of PMCA in all three WTD that received 300 ng of CWD+ brain (1307, #1316, #1303; FIG. 5, Tables 1 and 2). For both WTD dosed with 300 ng CWD+ saliva equivalent (#1309, #1313), as few as $6.25\times10^4$ buffy coat cells after 5 rounds of PMCA were required to detect positivity (FIG. 6, Tables 1 and 2).

The conventional readout for prion seeding activity generated by PMCA is western blot. Western blot analysis of PMCA round 5 product confirmed the presence of conversion competent protease K resistant prion protein in as few as $1.25×10^5$ buffy coat cells (FIG. 7), less than the minimum # of cells necessary for detection by PQ ($3.125×10^5$) in that deer (#1309).

Example 6—Prionemia Detection Improved at Higher LIQ Temperature

Figure 8:
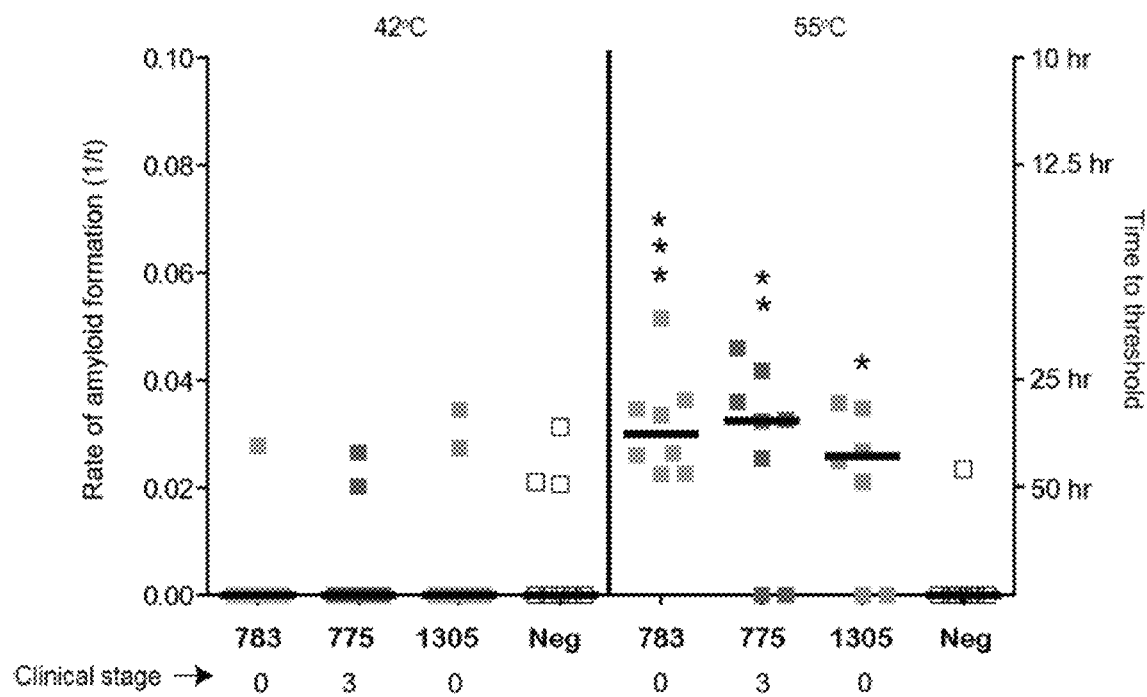
FIG. 8 is a graph showing that LIQ55 revealed prionemia in buffy coat cells from lymphoid biopsy CWD+ pre-clinical deer. Amyloid seeding activity was initially not detected in LIQ42 in pre-clinical animals #783 and #1305 or in #775 (Stage 3). Upon increasing the LIQ temperature to 55° C., all three samples demonstrated seeding activity (p<0.0128). Black lines represent the median of 8 replicates per deer (8 replicates shown). Statistical significance between infected and negative control deer is indicated with asterisks (p=0.0128-0.0006).

To determine if performing LIQ at 55° C. vs 42° C. would improve detection sensitivity, we assayed the three deer (#783, #775, #1305) that were negative by LIQ42 (FIG. 8). Upon assessment of $5×10^5$ buffy coat cells, LIQ55 permitted detection of amyloid seeding activity in all three deer (FIG. 8). These results, in addition to LIQ42 results, establish detection of hematogenous prions in 100% (14/14) of lymphoid biopsy positive WTD ranging in pre-clinical and clinical status Stage 0-Late 3. In particular, performing RT-QuIC at 55° C. vs 42° C. in the context of LIQ produced enhanced sensitivity.

Example 7—Prionemia Detection in Whole Blood

Briefly, 100 ul CPDA whole blood is combined with 2 ul iron oxide beads in a total of 1 ml PBS, which is followed by similar end-over-end incubation as per the LIQ protocol. Post end-over-end incubation the iron oxide beads are collected as in LIQ. The beads (in a variety of dilutions) are added to a sPMCA reaction for 1-5 rounds. Rounds 1-5 sPMCA product (3 ul) is analyzed for amyloid conversion by RT-QuIC assay as per LIQ.

Whole blood collection: Whole blood was collected in heparin (200 units $ml^{-1}$) and CPDA-1 (0.2 ml CPDA $ml^{-1}$ blood).

Iron oxide bead (IOB) treatment: After thawing, 100 ul whole blood resuspended in 900 ul PBS added to 2 µl IOB (49 mg $ml^{-1}$, ~9 µm; Bangs Laboratories, Indiana BioMag superparamagnetic iron oxide lot #10250) in a 1.7 ml tube. Samples were mixed end-over-end at room temperature for 30 min. Each sample was placed in a magnetic tray to recover the IOB fraction (magnetic particle separator, Pure Biotech, New Jersey). IOB were resuspended in 10 µl 0.1% SDS (sodium dodecyl sulfate, Sigma-Aldrich) and was further diluted 1:10 and 1:100 in PBS.

PMCA reactions: 10 ul of each dilution (neat, 1:10 and 1:100) of iron oxide bead concentrated/resuspended whole blood samples were sonicated for 60 sec, and spiked into 90 µl 10% NBH (w/v) in PCR microfuge tubes in single. Tubes were sonicated (30 sec every 29.5 min) for the first 72 h, then for 24 h rounds thereafter. After each round, 20 µl material was transferred into 50 µl fresh NBH and subjected to the next round for a total of 5 rounds (72 h first, then 4-24 h rounds). After 5 rounds, a 1:100 dilution of sample was analyzed by RT-QuIC.

Figure 9:
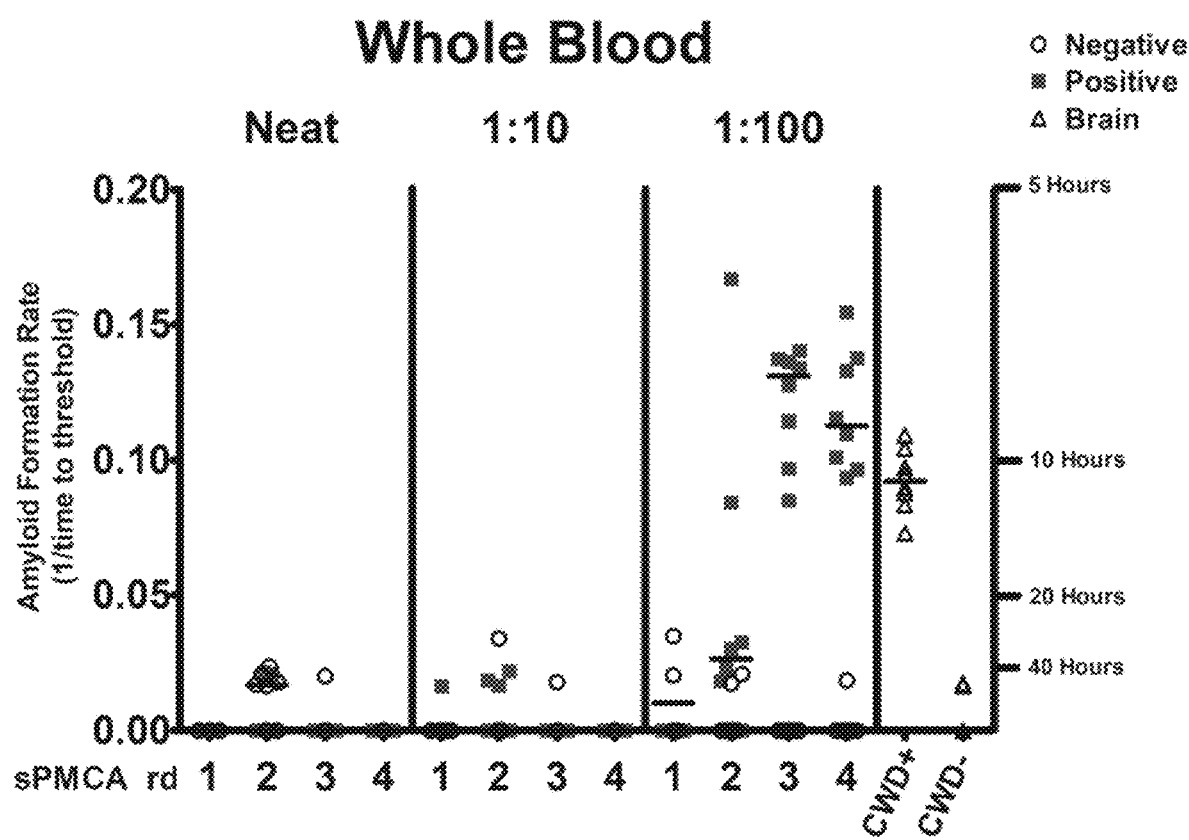
FIG. 9 is a graph depicting prionemia detection in whole blood.
Figure 14:
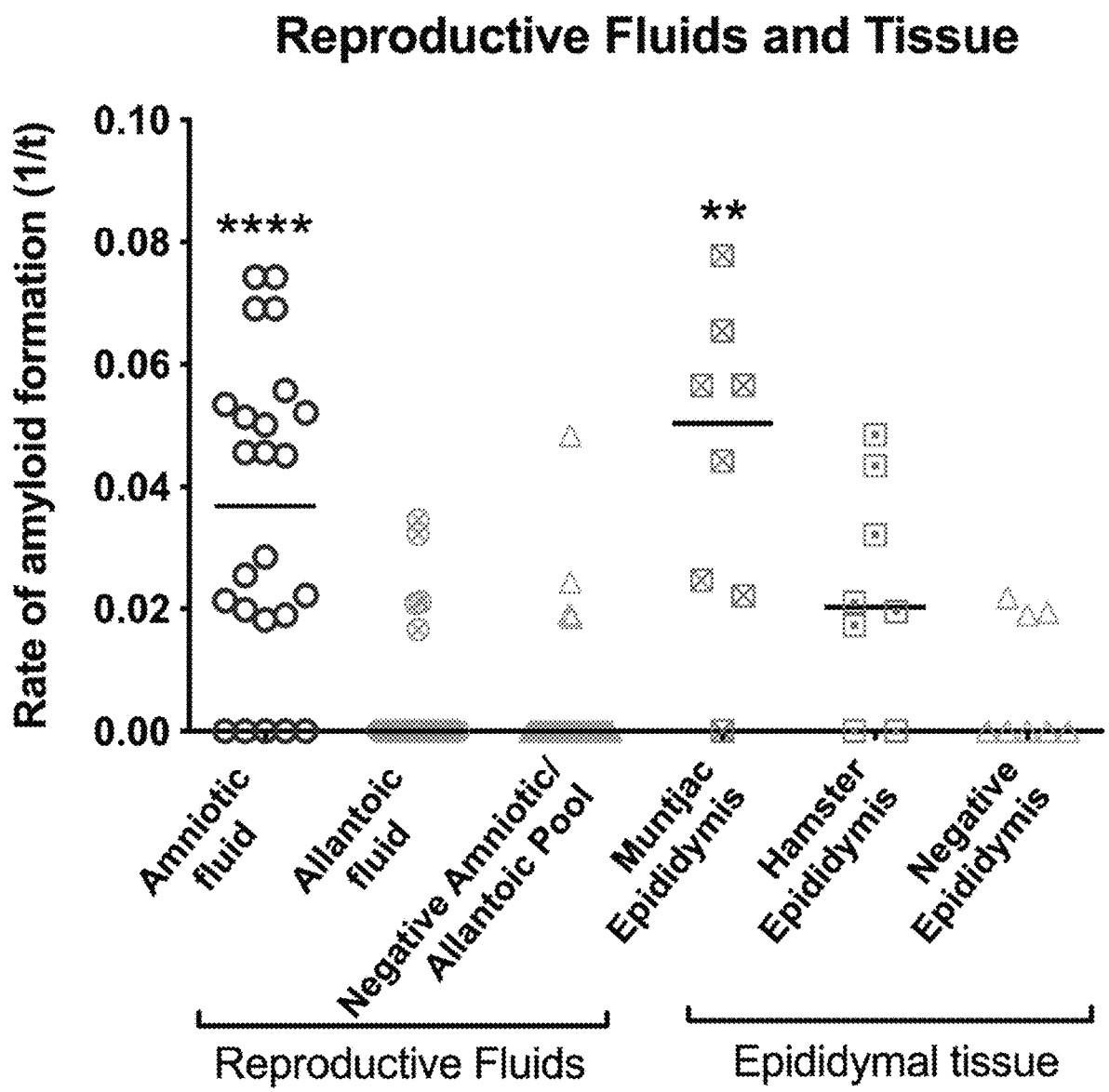
FIG. 14 is a graph showing amyloid seeding activity in amniotic fluid from pregnant subjects and male epididymis. The graph demonstrates the ability to detect amyloid in additional sample types using the methodology taught herein.
Figure 15:
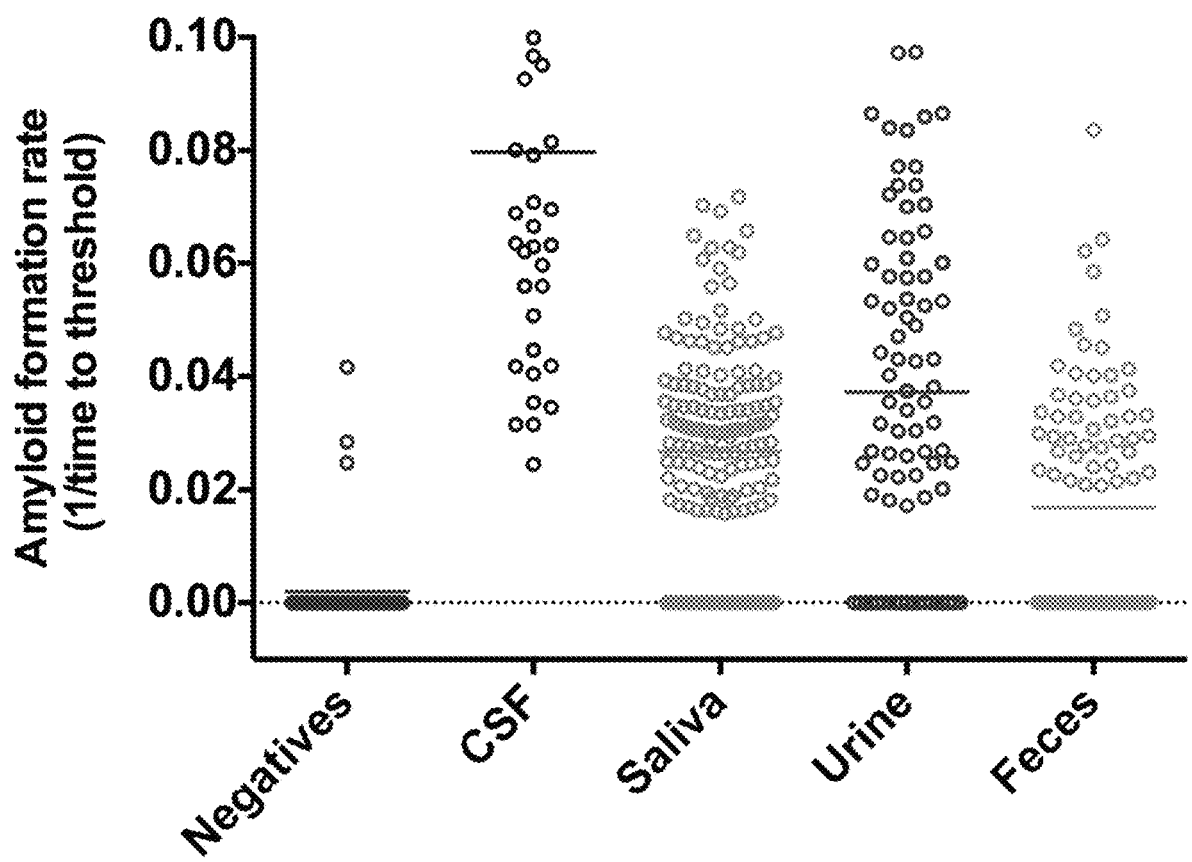
FIG. 15 is a graph showing that iron oxide bead/magnetic extraction (IOME) RT-QuIC can detect prion seeding activity from diverse heterogeneous biologic sources including body fluids, sections, and excretions. Represented here are samples from deer infection with chronic wasting disease (CWD). Negatives=uninfected animals. Methodology can also be applied to the prion diseases of other species.
Figure 17:
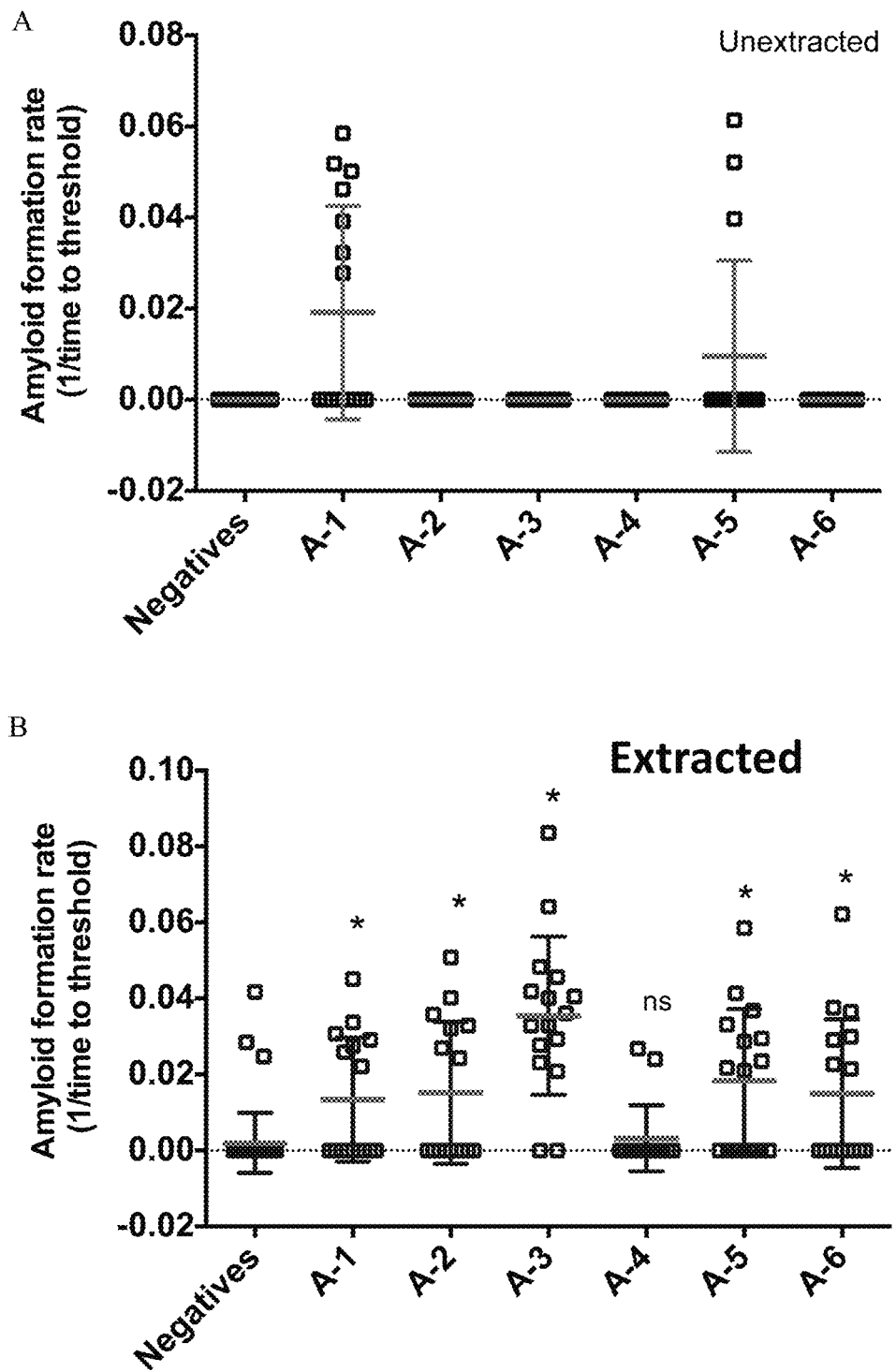
FIG. 17 is a set of two graphs showing that samples with high complexity and heterogeneous particulate matter, such as feces, can be analyzed via IOME-RT-QuIC. A-1 to A-6 represent individual CWD-infected animals from which deer feces were collected.
Figure 18:
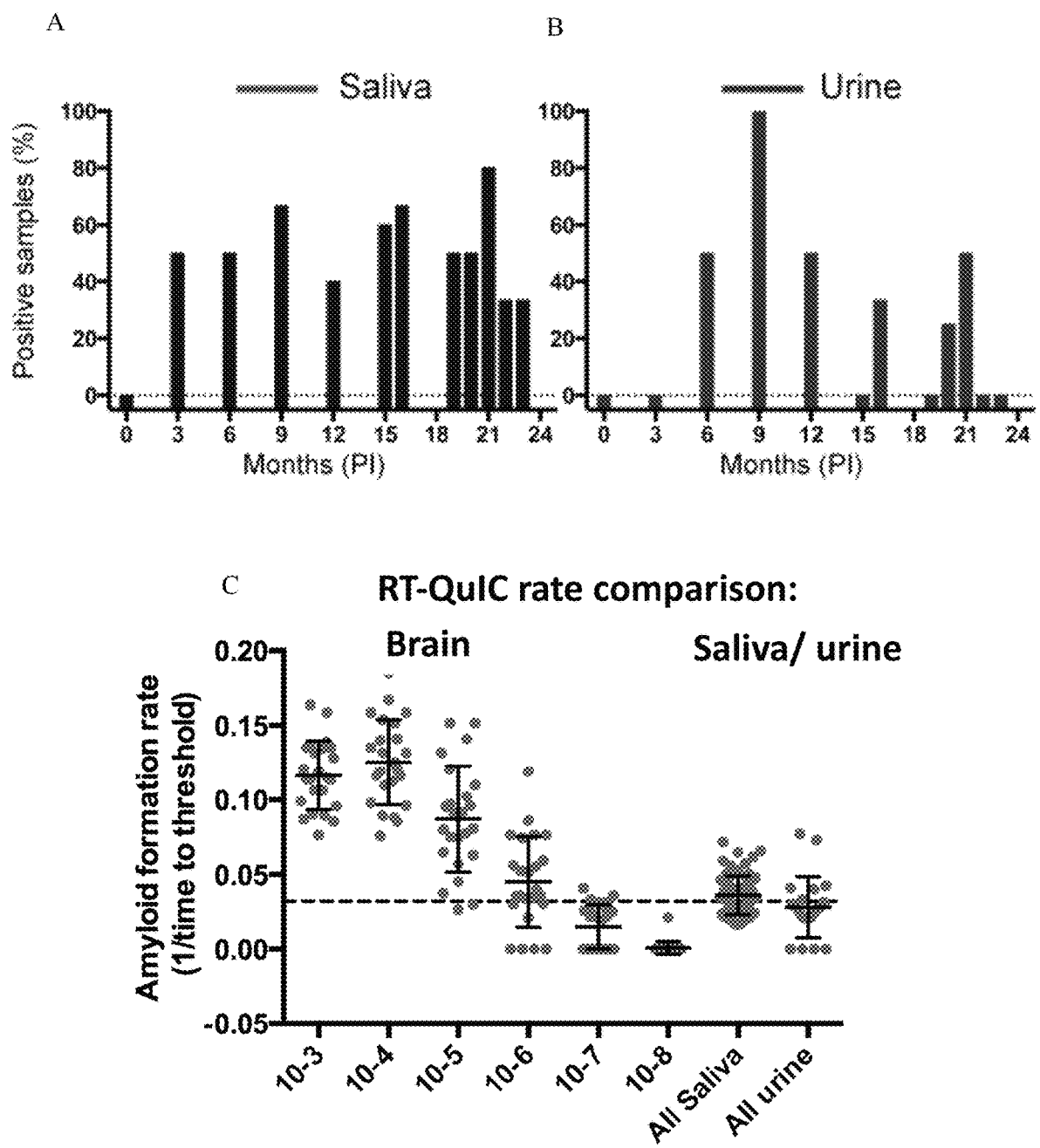
FIG. 18 is a set of three graphs showing longitudinal shedding of CWD prions in saliva and urine: detection and estimation of prion concentration by RT-QuIC.

RT-QuIC reactions: Each sample was plated 3 µl/well in quadruplicate in a 96 well plate (Greiner Bio-One optical bottom plate) containing 98 µl reaction mix (320 mM NaCl, 1.0 mM EDTA, 10 µM Thioflavin T (Sigma)) and placed in a FLUOstar Omega plate reader with 700 rpm double-orbital shaking for 50 h. The FLUOstar Omega reader collected fluorescence readings at 15 min intervals. CBP6 (CWD-positive) and 123 (CWD-negative) brain material were utilized as plate and assay controls. Samples were considered positive if they crossed a threshold (5 SD above the mean of the initial 5 readings). The inverse of the time when the reaction reached the threshold (1/time to threshold) was then used to determine the amyloid formation rate. Statistical analyses were run in Prism v6 (GraphPad Software, La Jolla, Calif.). A Mann-Whitney test was used to generate statistical significance (p-values <0.05 were considered significant) by comparing the sample rates to the rates of known negative control tissues. FIG. 9 is a graph depicting prionemia detection in whole blood. The methods for detection of prionemia in whole blood as disclosed herein also find application in the detection of prionemia in a wide variety of sample sources including urine, saliva, feces, cerebrospinal fluid, amniotic fluid, male reproductive fluids/seminal fluids and vaginal washes as demonstrated in FIG. 14 where the techniques are shown to work in samples of amniotic fluid from pregnant subjects and in samples collected from male epididymis. In addition, the methods for detection of prionemia have proven effective at detecting prionemia in saliva, feces, cerebrospinal fluid.

Example 8—Use of Blood-Borne Prion Amplification Assays for the Detection of Human Prion Diseases and Biomarker Assessment No practical noninvasive antemortem test previously exists to detect any prion disease. Low circulating amyloid concentrations in blood and the presence of blood-based inhibitors can interfere with consistent antemortem detection. Simple, rapid, specific and highly sensitive in vitro assays to detect blood-borne prions have been developed and are presented herein.

Through the use of ultrasensitive in vitro amplification assays (Lipase; Iron oxide bead; RT-QuIC-("LIQ"), and combined use of sPMCA with RT-QuIC readout ("PQ")), we have demonstrated the ability to detect low concentrations of blood-born prions is made possible as taught herein.

Figure 11:
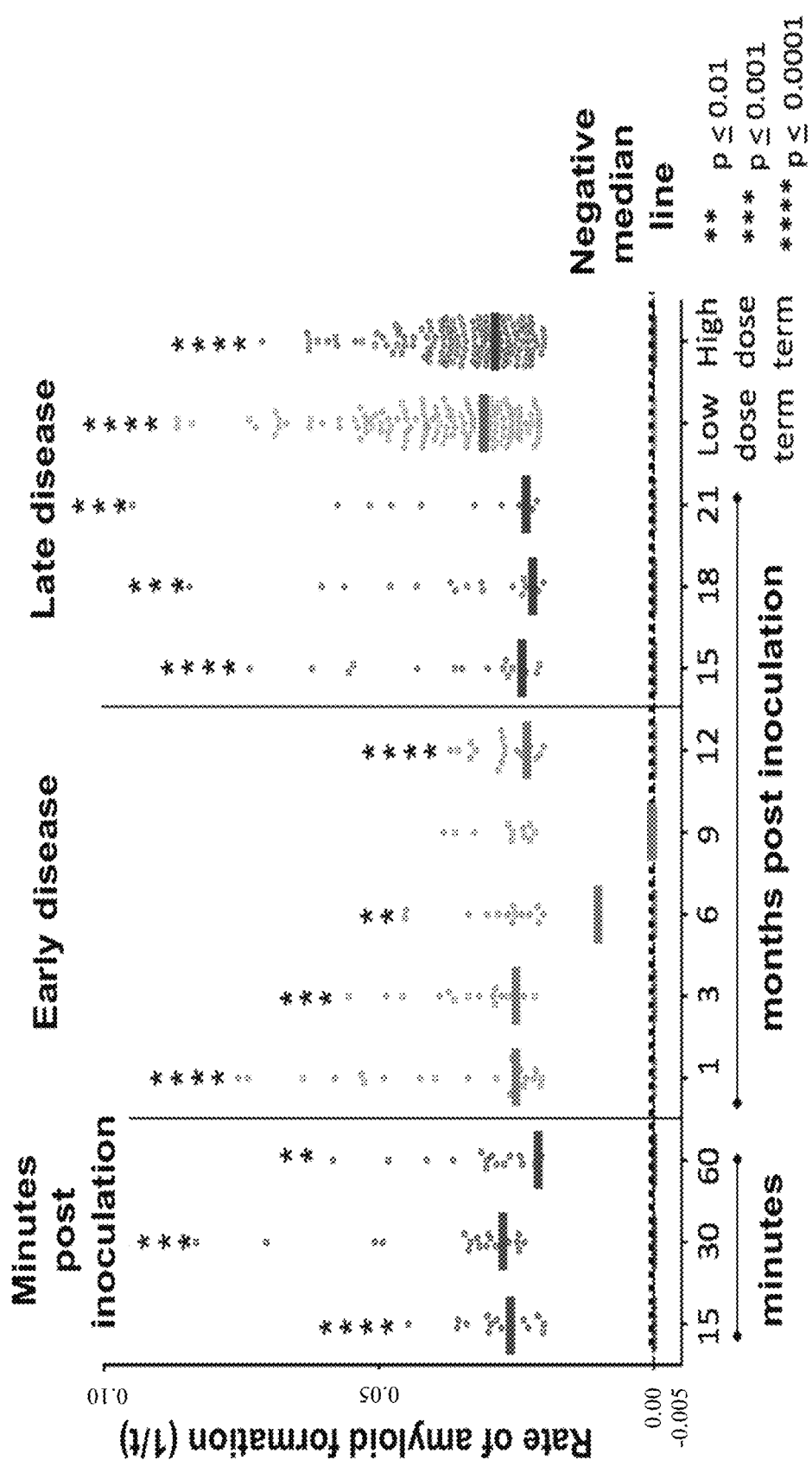
FIG. 11 is a graph depicting LIQ longitudinal detection of prionemia in cervids receiving oral low-dose CWD (n=8 deer).
Figure 12:
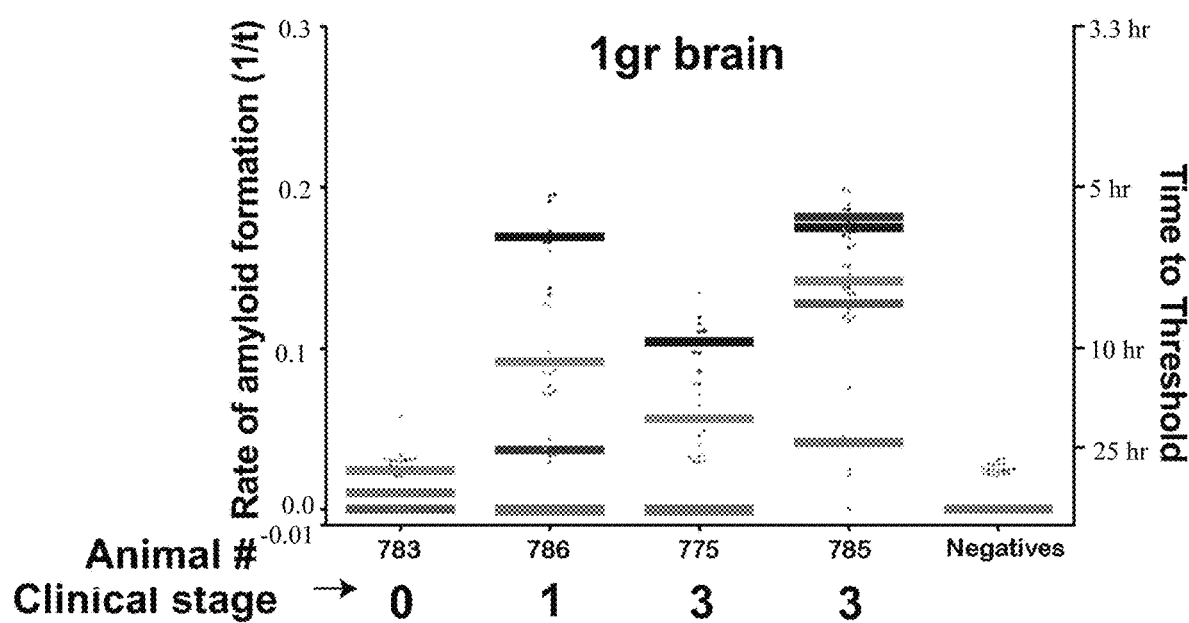
FIG. 12 is a pair of graphs depicting PQ detection of hematogenous prions in pre-clinical and clinical CWD+ cervids.
Figure 13:
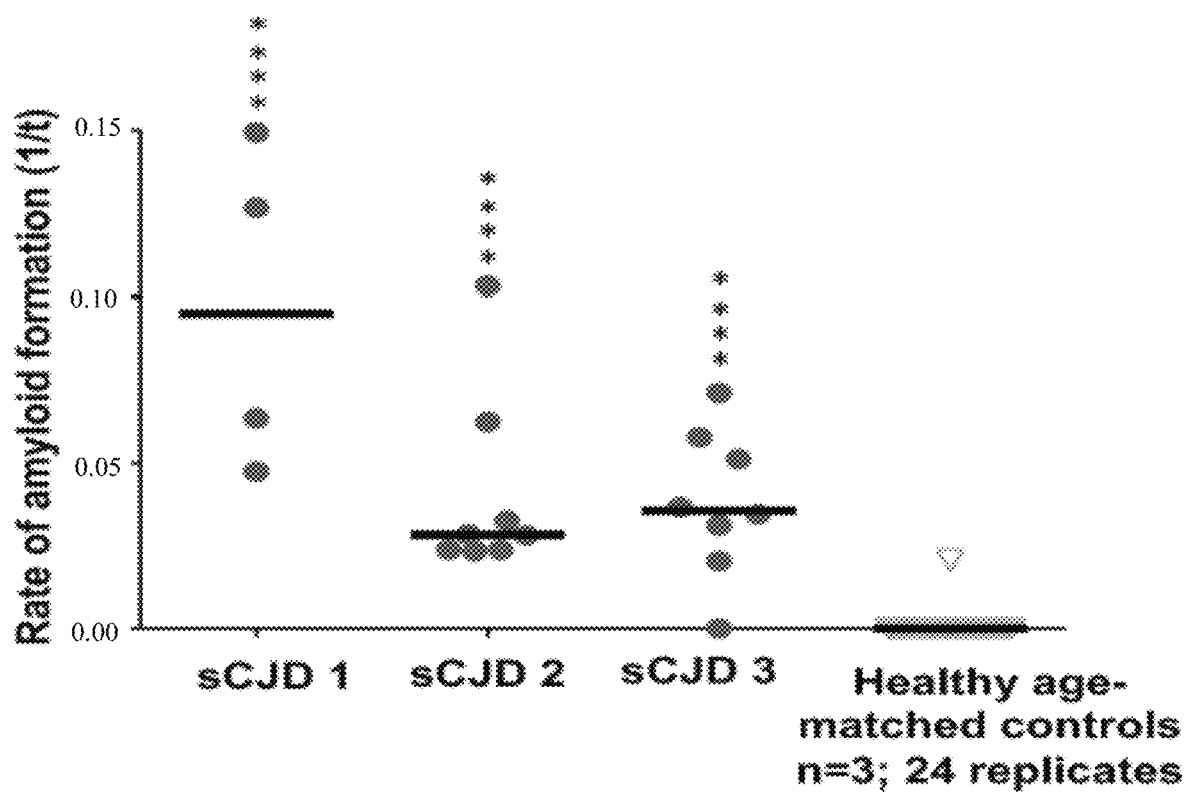
FIG. 13 is a graph depicting RT-QUIC LIQ detection of hematogenous prions in sCJD patients. The graph demonstrates the ability to detect amyloid in blood buffy coat cells collected from confirmed sporadic Cruetzfeldt-Jakob (sCJD) human patients vs no detection in healthy age-matched controls. The data was acquired using the LIQ55 RT-QuIC assay and $1 \times 10^6$ blood buffy coat cell input. The assay opens up the ability to detect amyloid in blood cells of patients with mutations that portend prion disease, such as in patients with Alzheimer's and Parkinson's disease.

Prion infectivity has been demonstrated in blood components of humans affected by sporadic and variant (s/v) CJD [Peden et al., *Lancet* 364, 527-529 (2004); Wroe et al., *Lancet* 368, 2061-2067 (2006); Orru et al., *PMBio* 2, e00078-00011 (2011)]. Yet, little is known about hematogenous amyloid forms or seeds in patients bearing genetic mutations that foretell for prion disease. We have developed unique methods to detect low concentrations of cervid chronic wasting disease (CWD) and hamster transmissible mink encephalopathy (TME) prions amid potent assay inhibitors in blood (FIGS. 11 and 12). We also present data herein demonstrating the ability of these assays to detect amyloid in blood components of sCJD patients (FIG. 13). We present the application of screening employing blood buffy coat cells from subjects with autopsy confirmed sCJD and genetic prion disease by LIQ and PQ to demonstrate the specificity and sensitivity of these assays to detect human prion disease. The assays taught herein will have application for the detection of active disease for use in diagnostics, human and animal surveillance and therapeutic trials. Using the techniques taught herein the amplification assays LIQ and PQ will detect human prion amyloid seeds in blood.

The techniques taught herein will allow for the determination of temporal prion status in longitudinal blood samples collected from patients with symptomatic prion disease and cross-sectional blood samples from known mutation carriers. Little is known about the hematogenous status of patients that carry genetic mutations that portend prion disease. Globally, these and other protein misfolding disorders with protracted time course lasting months to decades affect millions of humans [World Alzheimer Report 2018-Global Dementia. (2018). www.alz.co.uk]. Presumably, amyloid formation and accumulation responsible for these diseases begins years before clinical presentation, much like other prion diseases and human proteinopathies (e.g., Alzheimer's and Parkinson's disease). Using these novel methods, we demonstrate prionemia in buffy coat cells harvested from hosts minutes post-low dose oral prion-exposure through terminal clinical disease. Longitudinal blood samples collected from patients affected by sCJD and genetic mutations of prion disease, including asymptomatic genetic disease mutation carriers, can be used to asses disease status and the course of disease. This will provide a temporal profile of hematogenous prions in humans facilitating the use of associated biomarkers for prognostication and the development of therapeutic trials. It is submitted that blood components of mutation carriers harbor detectable prion amyloid seeds prior to symptom onset and that there is a measurable longitudinal change in seeding activity that is detectable by this assay.

Figure 10:
FIG. 10 is an illustration depicting the experimental design for the experiments as shown in FIG. 13.

Experimental Design: Using LIQ and PQ, serial buffy coat cells can be collected from humans affected by sCJD and prion mutation carriers for evidence of prions. (See e.g. FIG. 10)

Serial blood samples are collected from patients with known and suspect prion disease and mutation carriers that portend prion disease. Buffy coat (BC) cells from known age-matched healthy and CJD patients currently in −80° C. can be used as positive and negative controls.

Buffy Coat Isolation: Buffy coat ("BC") cells are collected from 10 ml CPDA-treated whole blood by centrifugation and treated with lyse buffer and phosphate buffered saline (PBS) washes to remove red blood cells. BC are aliquoted at $10^7$ cells/vial for storage at −80° C. A variety of sCJD samples can be chosen to reflect the natural distribution of sCJD molecular subtypes in the U.S. [Parchi et al., *Ann Neurol* 46, 224-233 (1999)]. Similarly, blood samples from a variety of genetic prion disease mutations can be assessed employing the methodology and compositions taught herein. The above facilitates the assessment of differences in assay sensitivity between human (and non-human animal) prion disease strains.

Amyloid conversion assays: Pos/neg controls are included in all assays. In vitro amyloid amplification assays require attention to mitigate cross contamination due to their ability to amplify small concentrations of prions to detectable levels.

Lipase Iron Oxide Bead (IOB) treatment: Samples are homogenized in a FastPrep homogenizer, diluted to $5\times10^5$ cells/ml in PBS with lipase B and lipase C (Sigma-Aldrich); 1 h, 37° C., mixing. The samples are added to 2 μl IOB (Bangs Laboratories, Indiana BioMag), and mixed end-over-end at room temp (rt) for 30 min. They are then placed in a magnetic tray to recover the IOB fraction, which is subsequently resuspended in 10 μl 0.1% SDS.

RT-QuIC: Each sample is plated in quadruplicate in a 96 well plate containing reaction mix (320 mM NaCl, 1.0 mM EDTA, 10 μM Thioflavin T) and placed in a FLUOstar plate reader for 50 h; fluorescence readings are measured at 15 min intervals. Statistical analyses can be run using Prism v6 (GraphPad Software, La Jolla, Calif.).

RT-QuIC rPrP substrate: Briefly, hamster (residues 90-234; accession AF156185) $rPrP^c$ can be utilized in the assays. $rPrP^C$ can be expressed and bound to Ni-NTA Superflow resin. The resin can be loaded onto and purified by FPLC column. Eluted protein can be dialyzed, and concentration determined by 280 nm absorbance. $rPrP^C$ can be frozen in aliquots at 0.4 mg/ml in −80° for use. [See: Henderson et al., *J Virol* 89, 9338-9347 (2015); Atarashi et al., *Nat Methods* 4, 645-650 (2007); Wilham et al., *PLoS Pathog* 6, e1001217 (2010)]

Data analysis: Quantitative analysis of blood component LIQ and PQ can be performed by the generation of a standard curve from prion+ human brain dilutional series fluorescence signal intensities. Signal intensity from non-amplified samples of known quantity can be plotted after subtraction of background and the line of best fit used to calculate signal decay-rate relative to increasing $PrP^{Sc}$ dilution. Samples can be considered positive if they cross a threshold (5 SD above the mean of the initial 5 readings). A Mann-Whitney test can be used to generate statistical significance (p-values <0.05 are considered significant) by comparing the sample rates to the rates of known negative control samples [McNulty et al., *PLoS One* 14, e0216621 (2019)].

sPMCA: Dilutions of samples can be sonicated for 60 sec and spiked into 90 μl 10% NBH (w/v) in PCR microfuge tubes in duplicate. Tubes can be sonicated (30 sec every 29.5 min) for the first 72 h, then for 24 h rounds thereafter. After each round, 20 μl material can be transferred into 50 μl fresh NBH for a total of 5 rounds (72 h first, then 4-24 h rounds). After 5 rounds, samples will be analyzed by a 1:100 dilution of sample in RT-QuIC.

sPMCA normal brain $PrP^C$ substrate (NBH): NBH (10% w/v) can be made using the FastPrep homogenizer from naïve Tg(HuPrP) overexpressing mice freshly perfused with PBS containing 5 mM EDTA. Each batch of NBH can consist of 3-6 mice, stored at −80° C. in single use aliquots.

The development of assays to detect blood-borne prions has been fraught with challenge because of presumed low circulating concentrations of prions in blood and the presence of blood-associated inhibitors. We have overcome these challenges by incorporating the use of lipase treatment coupled with iron oxide bead magnetic extraction prior to RT-QuIC (LIQ), and where advantageous, combining sPMCA and RT-QuIC (PQ) (FIGS. 11-13). The resultant robust assay systems now enable us to detect prions in serially-collected (15 mins-21 months pi) buffy coat cells of white-tailed deer exposed to low doses (300 ng) of CWD prions (FIGS. 11-13), a dose likely more consistent with natural exposures, and in buffy coat cells collected from human sCJD patients (FIG. 13).

Relevance to human prion disease: A rapid, sensitive specific blood assay for prions has been needed. Our assays have resulted in the development of corroborating assays with the capacity to overcome the presence of low circulating amyloid levels in blood and/or blood-associated inhibitors to demonstrate the presence of hematogenous prions (FIGS. 11-13). The application in human diagnosis and surveillance has not been previously possible. The detection of $PrP^C$-converting activity in the blood of sCJD patients is demonstrated herein (FIG. 13). The modified amyloid amplification assays, RT-QuIC LIQ and sPMCA with RT-QuIC readout (PQ) (FIGS. 11-13), can be used to analyze longitudinal collections of buffy coat cells from human s/v CJD and genetic mutation carriers of prion disease for the presence of $PrP^C$ converting activity.

Glossary of Claim Terms

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

The term "recombinant protein", or "recombinant PrP" refers to a protein/PrP encoded by a gene, a recombinant DNA, that has been cloned in a system that supports expression of the gene and translation of messenger RNA. Modification of the gene by recombinant DNA technology can lead to expression of a mutant protein. Proteins coexpressed in bacteria will not possess post-translational modifications, e.g. phosphorylation or glycosylation; eukaryotic expression systems are needed for proper post-translational modifications.

The term "recombinant DNA" refers to DNA sequences that result from the use of laboratory methods (molecular cloning) to bring together genetic material from multiple sources, creating sequences that would not otherwise be found in biological organisms.

The term "conformer" refers to a form of a compound having a particular molecular conformation. For example, the PrP protein can be folded as a non-pathogenic conformer (e.g. $PrP^C$, and $PrP^{sen}$) and a "mis-folded", pathogenic conformer (e.g. $PrP^D$, $PrP^{res}$, or $PrP^{Sc}$).

The term "conformational diseases" refers to that group of disorders arising from a propagation of an aberrant conformational transition of an underlying protein, leading to protein aggregation and tissue deposition. Such diseases can also be transmitted by an induced conformational change, propagated from a pathogenic conformer to its normal or non-pathogenic conformer and in this case they are called herein "transmissible conformational diseases". Examples of such kinds of diseases are the prion encephalopathies, including the bovine spongiform encephalopathy (BSE) and its human equivalent Creutzfeld-Jakob (CTD) disease, in which the underlying protein is the PrP.

The term "amyloid" refers to aggregates of proteins that become folded into a shape that allows many copies of that protein to stick together forming deposits, fibrils, tangles, or plaques.

The term "misfolded protein" refers to a protein that no longer contains all or part of the structural conformation of the protein as it exists when involved in its typical, non-pathogenic normal function within a biological system. Misfolded proteins may form aggregates that can be toxic. A misfolded protein may localize in protein aggregate. A misfolded protein may be a non-functional protein. A misfolded protein may be a pathogenic conformer of the protein. Monomeric, folded protein compositions may be provided in native, nonpathogenic confirmations without the catalytic activity for misfolding, oligomerization, and aggregation associated with seeds. Monomeric, folded protein compositions may be provided in seed-free form.

As used herein, "monomeric, folded protein" refers to single protein molecules. "Soluble, aggregated misfolded protein" refers to aggregations of monomeric, misfolded protein that remain in solution.

Monomeric and/or soluble, misfolded protein may aggregate to form insoluble aggregates and/or higher oligomers. For example, aggregation of Aβ protein may lead to protofibrils, fibrils, and eventually amyloid plaques that may be observed in AD subjects. "Seeds" or "nuclei" refer to soluble, misfolded protein or short fragmented fibrils, particularly soluble, misfolded protein with catalytic activity for further misfolding, oligomerization, and aggregation. Such nucleation-dependent aggregation may be characterized by a slow lag phase wherein aggregate nuclei may form, which may then catalyze rapid formation of further aggregates and larger polymers. The lag phase may be minimized or removed by addition of pre-formed nuclei or seeds. Monomeric protein compositions may be provided without the catalytic activity for misfolding and aggregation associated with seeds.

As used herein, aggregates of misfolded protein refer to non-covalent associations of protein including soluble, misfolded protein. Aggregates of misfolded protein may be "de-aggregated" or disrupted to break up or release misfolded protein. The catalytic activity of a collection of misfolded protein seeds may scale, at least in part with the number of seeds in a mixture. Accordingly, disruption of aggregates of misfolded protein in a mixture to release misfolded protein seeds may lead to an increase in catalytic activity for oligomerization of monomeric protein.

The methods may include contacting the sample with Thioflavin T and an excess of a monomeric, folded protein to form an incubation or reaction mixture. The methods may include conducting an incubation cycle two or more times effective to form an amplified portion of misfolded protein. Each incubation cycle may include incubating the incubation mixture effective to cause misfolding and/or aggregation of at least a portion of the monomeric, folded protein in the presence of the misfolded protein to form the amplified portion of the misfolded protein. Each incubation cycle may include shaking the incubation mixture effective to break up at least a portion of any protein aggregate present, e.g., to release the misfolded protein. The methods may also include determining the presence of the misfolded protein in the sample by detecting a fluorescence of the Thioflavin T corresponding to misfolded protein.

The term "prion" shall mean a transmissible particle known to cause a group of such transmissible conformational diseases (spongiform encephalopathies) in humans and animals. The term "prion" is a contraction of the words "protein" and "infection" and the particles are comprised largely if not exclusively of $PrP^{Sc}$ molecules.

Prions are distinct from bacteria, viruses and viroids. Known prions include those which infect animals to cause scrapie, a transmissible, degenerative disease of the nervous system of sheep and goats as well as bovine spongiform encephalopathies (BSE) or mad cow disease and feline spongiform encephalopathies of cats. Four prion diseases known to affect humans are (1) kuru, (2) Creutzfeldt-Jakob Disease (CJD), (3) Gerstmann-Strassler-Scheinker Disease (GSS), and (4) fatal familial insomnia (FFI). As used herein prion includes all forms of prions causing all or any of these diseases or others in any animals used and in particular in humans and in domesticated farm animals.

Protein Misfolding Cyclic Amplification, or "PMCA" is a technique that amplifies the prion disease-associated isoform of prion protein ($PrP^D$) in a sample by mixing the sample with an excess of the normal, non-pathogenic isoform of prion protein ($PrP^C$). The technique generally employs multiple rounds of amplification and disaggregation of the resulting product. More specifically, the starting $PrP^D$ in the sample, if any, converts the $PrP^C$ in the reaction mix to aggregates of the misfolded $PrP^D$ during the amplification phase of incubation. The resulting aggregates of $PrP^D$ are then dispersed, such as by sonication, to break up the aggregates into smaller chains. These smaller units of $PrP^D$ are then able to convert more of the $PrP^C$ in the sample into further aggregates of $PrP^D$. Brain homogenate from an uninfected animal is often used as the source of the $PrP^C$.

Serial Protein Misfolding Cyclic Amplification, or "sPMCA", is a modification of the PMCA technique whereby additional, fresh $PrP^C$ is added to the reaction mix after a number of rounds of amplification to prime additional conversion and boost the amplification of the $PrP^D$ in the sample. Seeded PMCA replaced the brain homogenate as the source of the $PrP^C$ with a recombinant $PrP^{sen}$.

Quaking Induced Conversion, or "QuIC", is a further modification of prior $PrP^D$ amplification techniques, using shaking of the reaction mix instead of sonication. Quaking Induced Conversion in its standard form employed tube-based reactions mixes, with the subsequent immunoblotting detection of the resulting $PrP^{res}$ product.

Heparin is a naturally occurring mucopolysaccharide that acts in the body as an antithrombin factor to prevent intravascular clotting. The substance is produced by basophils and mast cells, which are found in large numbers in the connective tissue surrounding capillaries, particularly in the lungs and liver. In the form of sodium salt, heparin is used therapeutically and in blood collection procedures as an anticoagulant. Heparin acts primarily through a complex that it forms with antithrombin III. This complex accelerates the inhibition of thrombin and activated Factor X to prevent clotting or activation of thrombin, which in turn prevents the formation of fibrin from fibrinogen. The source of heparin is usually either bovine or porcine lungs and intestines. Samples can be collected in heparinized tubes or heparin can be added to a sample. Common concentrations are 2 units per mL, 10 units per mL, 50 units per mL, 100 units per mL, or 200 units per mL.

The phrase "an excess of a non-pathogenic conformer" of a substrate (e.g. native conformation recombinant tau or alpha-synuclein protein), or a like phrase, refers to providing a sufficient amount of substrate such that a minute or undetectable level of misfolded seed protein in a sample can be amplified to detectable levels by having a sufficient quantity of the substrate to achieve at least such detectable levels.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y.; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); and Ausubel et al., Short Protocols in Molecular Biology (1999) 4th Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.).

Abbreviations used herein include:

CNS for central nervous system;

BSE for bovine spongiform encephalopathy;

CJD for Creutzfeldt-Jakob Disease;

CWD for chronic wasting disease (CWD);

CDPA for citrate phosphate dextrose adenine;

EDTA for ethylenediaminetetraacetic acid;

IHC for immunohistochemistry;

NaPTA for sodium phosphotungstic acid;

PMCA for protein misfolding cyclic amplification;

PrP for prion protein;

Tau is a microtubule associate protein rich in brain cells (neurons). Perturbations of this protein are associated with human neurodegenerative diseases, notably Alzheimer's Disease, traumatic brain injury, and other dementias;

Alpha synuclein is a protein rich in the sensor regions of neurons (synaptic vesicles) that are associated with signal transmission;

$PrP^C$ for the normal, non-pathogenic isoform of prion protein. This is sometimes referred to elsewhere as $PrP^{sen}$ as the prion protein is sensitive to protease digestion;

$PrP^D$ for the prion disease-associated isoform of prion protein. This is sometimes referred to elsewhere as $PrP^{res}$ as the prion protein is resistant to protease digestion or $PrP^{Sc}$ for the pathogenic or "scrapie" isoform of PrP;

$PrP^{Sc}$ for the pathogenic or "scrapie" isoform of PrP (which is also the marker for prion diseases);

QUIC for quaking-induced conversion assay;

rPrP for recombinant prion protein;

RT-QuIC for real-time quaking-induced conversion assay;

sPMCA for serial protein misfolding cyclic amplification;

ThT for thioflavin T;

TSE for transmissible spongiform encephalopathy;

vCJD for Variant Creutzfeldt-Jakob disease.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

TABLE 1

Study cohorts. Description of white-tailed deer study cohorts including: inoculum cohort, codon 96 genotype, clinical disease status, CWD amyloid seeding assay status, and minimum number of buffy coat cells required to reach statistical significance after PQ on 5 rounds of PMCA.

| Inoculum | Deer # (codon 96) | Clinical Stage at termination (out of 4) | LIQ 42 | LIQ 55 | PQ and statistical significance |
|---|---|---|---|---|---|
| 1 g CWD+ brain (1 dose PO) | 783 (GS) | 0 | Negative | Positive | Negative |
| | 786 (GG) | 0 | Positive | NA | $6.25 \times 10^4$ *** |
| | 775 (GS) | Late 3 | Negative | Positive | $3.125 \times 10^4$ *** |
| | 784 (GG) | Late 3 | Positive | NA | ND |
| | 782 (GG) | Late 3 | Positive | NA | ND |
| | 785 (GG) | Late 3 | Positive | NA | $3.125 \times 10^4$ *** |

TABLE 1-continued

Study cohorts. Description of white-tailed deer study cohorts including: inoculum cohort, codon 96 genotype, clinical disease status, CWD amyloid seeding assay status, and minimum number of buffy coat cells required to reach statistical significance after PQ on 5 rounds of PMCA.

| Inoculum | Deer # (codon 96) | Clinical Stage at termination (out of 4) | LIQ 42 | LIQ 55 | PQ and statistical significance |
|---|---|---|---|---|---|
| 1 mg CWD+ brain (1 dose PO) | 1305 (GS) | 0 | Negative | Positive | $2.5 \times 10^5$ *** |
| | 1310 (GS) | 0 | Positive | NA | $3.125 \times 10^4$ * |
| | 1308 (GG) | Late 3 | Positive | NA | $1.25 \times 10^5$ *** |
| 300 ng CWD+ brain | 1307 (GS) | 0 | Positive | NA | $6.25 \times 10^4$ * |
| | 1316 (GG) | 2 | Positive | NA | $3.125 \times 10^4$ *** |
| (100 ng × 3 doses) Saliva (10 ml × 3 doses; RT-QuIC equivalent to 300 ng CWD + brain) | 1303 (GG) | Late 3 | Positive | NA | $3.125 \times 10^4$ *** |
| | 1309 (GG) | 2 | Positive | NA | $6.25 \times 10^4$ *** |
| | 1313 (GG) | Early 3 | Positive | NA | $6.25 \times 10^4$ * |

TABLE 2

Statistical significance of RT-QuIC amyloid formation rates following PMCA rounds 1-5 (PQ) initiated with buffy coat cell amounts ranging from $1 \times 10^6$-$3.125 \times 10^4$. Statistical analysis was performed after each round and P value was calculated.

| | | | Dilution | | | | | | | | | | |
|---|---|---|---|---|---|---|---|---|---|---|---|---|---|
| | | | $1 \times 10^6$ | | $5 \times 10^5$ | | $2.5 \times 10^5$ | | $1.25 \times 10^5$ | | $6.25 \times 10^4$ | | $3.125 \times 10^4$ | |
| Inoculum | Deer # | PMCA Round | Sig | P Value | Sig | P Value | Sig | P Value | Sig | P Value | Sig | P Value | Sig | P Value |
| 1 g CBP6 (1 dose PO) | 783 | R1 | ns | 0.3654 | ns | 0.0732 | ns | 0.1301 | ns | 0.8488 | ns | 0.3073 | ** | 0.0085 |
| | | R2 | ns | 0.2516 | ns | 0.5399 | ns | NA | ns | 0.6353 | ns | 0.2953 | ns | NA |
| | | R3 | ns | 0.6137 | ns | 0.6472 | ns | 0.9575 | ns | NA | ns | 0.909 | ns | 0.4689 |
| | | R4 | ns | 0.957 | ns | 0.1332 | ns | 0.4794 | ns | 0.9575 | ns | 0.4228 | ns | 1 |
| | | R5 | ns | 0.5871 | ns | 0.1313 | ns | 0.884 | ns | 0.9418 | ns | 0.2953 | ns | 0.909 |
| | 786 | R1 | ns | 0.0848 | ns | 0.8504 | ns | 0.9679 | ns | 0.4636 | ns | 0.9696 | ns | 0.9575 |
| | | R2 | ns | 0.0848 | ns | 0.9575 | ns | 0.909 | ns | 0.2373 | ns | 0.4688 | ns | 0.6202 |
| | | R3 | * | 0.0499 | *** | 0.0001 | *** | 0.0003 | ns | NA | *** | 0.0002 | ns | 0.8405 |
| | | R4 | *** | 0.0002 | *** | 0.0001 | *** | 0.0001 | ns | 0.9575 | *** | 0.0001 | ns | 0.517 |
| | | R5 | *** | 0.0002 | *** | 0.0001 | *** | 0.0001 | ns | 0.1158 | *** | 0.0001 | ns | 0.0845 |
| | 775 | R1 | ns | 0.0848 | ns | 0.5752 | ns | NA | ns | 0.5178 | ns | 0.6202 | ns | 0.4794 |
| | | R2 | ns | 0.2716 | ns | 0.9575 | ns | 0.4656 | ns | NA | ns | 0.7896 | ns | NA |
| | | R3 | ns | 0.2716 | ns | 0.8553 | ns | NA | ns | NA | ns | 0.7781 | * | 0.0378 |
| | | R4 | * | 0.0379 | *** | 0.0001 | ns | 0.9575 | ns | 0.604 | ** | 0.0031 | *** | 0.0001 |
| | | R5 | *** | 0.0002 | *** | 0.0001 | ns | 0.2752 | * | 0.0418 | ns | 0.1012 | *** | 0.0001 |
| | 785 | R1 | * | 0.0219 | *** | 0.0003 | *** | 0.0001 | *** | 0.0001 | *** | 0.0001 | ** | 0.0054 |
| | | R2 | *** | 0.0002 | *** | 0.0001 | *** | 0.0001 | *** | 0.0001 | *** | 0.0001 | ** | 0.0016 |
| | | R3 | *** | 0.0002 | *** | 0.0001 | *** | 0.0001 | ns | NA | *** | 0.0001 | *** | 0.0007 |
| | | R4 | *** | 0.0002 | *** | 0.0001 | *** | 0.0001 | *** | 0.0001 | *** | 0.0001 | ns | 0.274 |
| | | R5 | *** | 0.0002 | *** | 0.0001 | *** | 0.0001 | *** | 0.0001 | *** | 0.0001 | *** | 0.0005 |
| 1 mg CBP6 (1 dose PO) | 1305 | R1 | ns | 0.5871 | ns | 0.0732 | ns | 0.1347 | * | 0.0152 | ns | 0.1939 | ns | 0.4228 |
| | | R2 | ns | 0.3854 | ns | 0.9575 | ns | 0.4656 | ns | 0.516 | ns | 0.4688 | ns | 0.8405 |
| | | R3 | ns | 0.1652 | ns | 0.8054 | ns | 0.9575 | ns | NA | ns | 0.4127 | ns | 0.7781 |
| | | R4 | ns | 0.7059 | ns | 0.5975 | ns | 0.1313 | ns | 0.604 | * | 0.0486 | ns | 0.2752 |
| | | R5 | ns | 0.4881 | *** | 0.0001 | *** | 0.0002 | ns | 0.4688 | ns | 0.7773 | ns | 0.8488 |
| | 1310 | R1 | ns | 0.2516 | ns | 0.5752 | ns | 0.8488 | ns | 0.8405 | ns | 0.3385 | ns | 0.2444 |
| | | R2 | ns | 0.8694 | ns | 0.2112 | ns | 0.4688 | ns | 0.5611 | ns | 1 | ns | 0.1489 |
| | | R3 | ns | 0.1501 | ns | 0.4436 | ns | 0.0835 | ns | NA | ns | 0.7781 | ns | 0.9679 |
| | | R4 | *** | 0.0002 | ns | 0.1825 | ns | 0.9575 | * | 0.0145 | * | 0.0269 | ns | 0.6615 |
| | | R5 | *** | 0.0002 | *** | 0.0004 | *** | 0.0003 | ** | 0.0069 | ** | 0.0013 | * | 0.011 |

TABLE 2-continued

Statistical significance of RT-QuIC amyloid formation rates following PMCA rounds 1-5 (PQ) initiated with buffy coat cell amounts ranging from $1 \times 10^6$-$3.125 \times 10^4$. Statistical analysis was performed after each round and P value was calculated.

| Inoculum | Deer # | PMCA Round | Dilution | | | | | | | | | | | |
|---|---|---|---|---|---|---|---|---|---|---|---|---|---|---|
| | | | $1 \times 10^6$ | | $5 \times 10^5$ | | $2.5 \times 10^5$ | | $1.25 \times 10^5$ | | $6.25 \times 10^4$ | | $3.125 \times 10^4$ | |
| | | | Sig | P Value | Sig | P Value | Sig | P Value | Sig | P Value | Sig | P Value | Sig | P Value |
| | 1308 | R1 | ns | 0.5069 | *** | 0.0002 | ns | 0.4636 | *** | 0.0001 | *** | 0.0002 | ns | 0.604 |
| | | R2 | *** | 0.0002 | *** | 0.0001 | ns | 0.4222 | *** | 0.0001 | ns | 0.7514 | ns | 0.4636 |
| | | R3 | *** | 0.0002 | *** | 0.0001 | * | 0.0269 | ns | NA | ns | 0.6353 | ns | 0.4127 |
| | | R4 | *** | 0.0002 | *** | 0.0001 | *** | 0.0001 | *** | 0.0001 | ns | 0.4794 | ns | 0.2953 |
| | | R5 | *** | 0.0002 | *** | 0.0001 | *** | 0.0001 | *** | 0.0001 | ns | NA | ns | 0.7781 |
| 300 ng CBP6 (100 ng × 3 doses) | 1307 | R1 | ns | 0.1389 | * | 0.0131 | * | 0.0448 | ns | 0.1489 | ns | 0.0664 | ** | 0.0015 |
| | | R2 | ns | 0.1652 | ** | 0.0068 | ns | 0.909 | ns | 0.6353 | * | 0.0355 | ns | 0.0726 |
| | | R3 | ns | 0.7875 | ns | 0.0664 | ns | 0.1814 | ns | NA | ns | 0.1301 | ns | NA |
| | | R4 | ns | 0.8715 | ns | 0.2428 | ns | 0.1107 | * | 0.0434 | ** | 0.0085 | ns | 0.0769 |
| | | R5 | ns | 0.4881 | ns | 0.1814 | ns | 0.9418 | ns | 0.6615 | * | 0.0411 | ns | 0.909 |
| | 1316 | R1 | ns | NA | ns | 0.8504 | ns | NA | ns | 0.4127 | ns | NA | ns | NA |
| | | R2 | ns | NA | * | 0.0401 | ns | 0.6615 | ns | 0.2084 | ns | 0.2598 | ns | 0.4234 |
| | | R3 | ns | NA | ns | 0.2169 | *** | 0.0001 | ns | NA | ns | 0.6202 | ns | 0.2901 |
| | | R4 | * | 0.0496 | *** | 0.0001 | *** | 0.0001 | ns | 0.604 | * | 0.0486 | ** | 0.0049 |
| | | R5 | ns | 0.9491 | *** | 0.0001 | *** | 0.0001 | ns | 0.7316 | ns | 0.7773 | *** | 0.0001 |
| | 1303 | R1 | ns | 0.6946 | *** | 0.0001 | *** | 0.0001 | ns | 0.1489 | ** | 0.0002 | *** | 0.0002 |
| | | R2 | ns | 0.1455 | *** | 0.0001 | *** | 0.0001 | *** | 0.0002 | ** | 0.003 | *** | 0.0008 |
| | | R3 | *** | 0.0002 | *** | 0.0001 | *** | 0.0001 | ns | NA | ** | 0.0084 | ns | 0.098 |
| | | R4 | *** | 0.0002 | *** | 0.0001 | *** | 0.0001 | *** | 0.0001 | ns | 0.4794 | ns | 0.9696 |
| | | R5 | *** | 0.0002 | *** | 0.0001 | *** | 0.0001 | *** | 0.0001 | ** | 0.0013 | *** | 0.0002 |
| Saliva (10 ml × 3 doses; RT-QuIC equivalent to 300 ng CBP6) | 1309 | R1 | ns | 0.0946 | *** | 0.0002 | ** | 0.0037 | *** | 0.0001 | ns | 0.2598 | * | 0.0269 |
| | | R2 | ** | 0.0047 | *** | 0.0001 | *** | 0.0001 | *** | 0.0001 | ns | 0.8488 | ns | 0.8405 |
| | | R3 | *** | 0.0002 | *** | 0.0001 | *** | 0.0001 | ns | NA | ns | 0.675 | ns | 0.1548 |
| | | R4 | *** | 0.0002 | *** | 0.0001 | *** | 0.0001 | *** | 0.0001 | ns | 0.604 | ns | 0.6615 |
| | | R5 | *** | 0.0002 | *** | 0.0001 | *** | 0.0001 | *** | 0.0001 | *** | 0.0001 | ns | 0.7316 |
| | 1313 | R1 | *** | 0.0002 | ns | NA | ** | 0.0019 | ns | 0.0529 | ns | NA | ns | NA |
| | | R2 | *** | 0.0002 | ns | NA | ns | 0.6095 | ns | 0.8603 | ns | 0.2598 | ns | 0.2901 |
| | | R3 | *** | 0.0002 | ns | 0.1584 | ns | NA | ns | NA | ns | NA | ns | 0.4127 |
| | | R4 | *** | 0.0002 | * | 0.0393 | ns | 0.0585 | ns | 0.9575 | ns | 0.4794 | ns | 0.6095 |
| | | R5 | *** | 0.0002 | ns | 0.9575 | *** | 0.0001 | ** | 0.0011 | * | 0.0343 | ns | 0.0813 |

Asterisks and shading indicate significance level of low to high, or light to dark (ns = not significant, p > 0.05).

What is claimed is:

1. A method of sample processing comprising the steps of:
providing a sample to be processed for the detection or quantification of prion disease-associated isoform of prion protein ($PrP^D$), wherein the sample is a buffy coat cell fraction of a blood sample;
performing lipase treatment on the sample;
contacting the lipase-treated sample with magnetic iron oxide beads (IOBs), whereby the IOBs bind $PrP^D$ in the sample;
recovering the IOBs from the lipase-treated sample;
resuspending the recovered IOBs having the bound $PrP^D$; and
performing real time quaking induced conversion on the processed sample at about 55° C. or higher.

2. The method according to claim 1 wherein the blood sample is collected in an anticoagulant.

3. The method according to claim 2 wherein the anticoagulant is heparin or citrate phosphate dextrose adenine (CPDA).

4. The method according to claim 1 wherein the lipase treatment is performed with lipase B or lipase C.

5. The method according to claim 1 further comprising the step of performing protein misfolding cyclic amplification (PMCA) on the processed sample.

6. The method according to claim 1 further comprising the steps of:

amplifying the processed sample using protein misfolding cyclic amplification (PMCA); and analyzing the amplified sample using real time quaking induced conversion readout.

7. The method according to claim 6 wherein 5 or more rounds of PMCA are performed.

8. The method according to claim 6 wherein 2 or more rounds of PMCA, 3 or more rounds of PMCA are performed, or 4 or more rounds of PMCA are performed.

9. The method according to claim 1 further comprising the steps of:

collecting a blood sample from a subject in an anticoagulant; and recovering the buffy coat cell fraction of collected blood sample.

10. The method according to claim 9 wherein the sample is collected from a pre-clinical subject or a subject not showing symptoms of infection with a pathogenic conformer of a prion protein.

11. A method for the amplification of prion disease-associated isoform of prion protein ($PrP^D$) in a sample comprising the steps of:

providing a sample having $PrP^D$ or a sample to be screened for the presence of $PrP^D$;

performing lipase treatment of the sample;

contacting the lipase-treated sample with magnetic iron oxide beads (IOBs), whereby the IOBs bind $PrP^D$ in the sample;

recovering the IOBs from the lipase-treated sample;

providing a reaction mixture comprising an excess of normal, non-pathogenic isoform of prion protein ($PrP^C$);

combining the reaction mix and the recovered IOBs;

incubating the reaction mixture at about 55° C. or higher under conditions effective to cause misfolding or aggregation of the $PrP^C$ in the combined reaction mixture;

disaggregating any aggregates of $PrP^D$ formed during the incubating step; and repeating the incubating and disaggregating steps one or more times to produce an amplified $PrP^D$ in the reaction mixture.

12. The method according to claim 11 further comprising the steps of:

incubating the reaction mixture in the presence of thioflavin-T under conditions effective to cause aggregation of the $PrP^D$ in the reaction mixture and binding of the thioflavin-T to the resulting aggregates; and measuring the fluorescence in the reaction mixture, whereby the fluorescence in the reaction mixture is indicative of the presence or amount of $PrP^D$ in the sample to be screened for the presence of $PrP^D$.

13. The method according to claim 12 further comprising the steps of:

comparing the fluorescence in the reaction mix to the fluorescence in a standard curve of known concentration of $PrP^D$; and computing the amount of $PrP^D$ in the sample based upon the comparison.

14. The method according to claim 11 wherein the aggregates are disaggregated by a technique selected from the group consisting of sonication, stirring, shaking, freezing/thawing, laser irradiation, high pressure, homogenization, and cyclic agitation.

15. The method according to claim 11 wherein the sample is a sample selected from the group consisting of urine, saliva, feces, cerebrospinal fluid, amniotic fluid, male reproductive fluids, seminal fluids and vaginal washes.

16. A method for the detection of a prion disease-associated isoform of prion protein ($PrP^D$) in a blood sample comprising the steps of:

collecting a whole blood sample to be processed for the screening of $PrP^D$;

performing lipase treatment of the sample;

performing metal bead extraction on the lipase-treated sample using magnetic iron oxide beads (IOBs);

recovering the bead fraction of the sample;

amplifying the $PrP^D$ in the sample using a plurality of rounds of protein misfolding cyclic amplification (PMCA) reactions with substrate;

combining the amplified sample with Thioflavin T;

re-amplifying the sample using a real-time quaking-induced conversion assay (RT-QuIC) reaction at about 55° C. or higher; and detecting the presence of $PrP^D$ in the whole blood sample by measuring the resulting fluorescence in the sample.

17. The method according to claim 16 wherein the sample is a buffy coat cell fraction from a blood sample.

18. A method for the detection of a prion disease-associated isoform of prion protein ($PrP^D$) in a blood sample comprising the steps of:

providing a buffy coat cell fraction of a blood sample;

performing lipase treatment of the buffy coat cell fraction;

contacting the lipase-treated buffy coat cell fraction with magnetic iron oxide beads (IOBs);

recovering the IOB fraction of the lipase-treated sample;

amplifying the $PrP^D$ in the sample using a plurality of rounds of protein misfolding cyclic amplification (PMCA) reactions;

combining the amplified sample with Thioflavin T;

re-amplifying the sample using a real-time quaking-induced conversion assay (RT-QuIC) reaction at about 55° C. or higher; and detecting the presence of $PrP^D$ in the sample by measuring the resulting fluorescence in the sample.

\* \* \* \* \*